(12) United States Patent
Mori et al.

(10) Patent No.: US 11,026,661 B2
(45) Date of Patent: Jun. 8, 2021

(54) IMAGING APPARATUS FOR DIAGNOSIS AND PROGRAM

(71) Applicant: TERUMO KABUSHIKI KAISHA, Tokyo (JP)

(72) Inventors: Isao Mori, Chofu (JP); Ema Itoh, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1588 days.

(21) Appl. No.: 14/873,638

(22) Filed: Oct. 2, 2015

(65) Prior Publication Data
US 2016/0022248 A1     Jan. 28, 2016

Related U.S. Application Data

(63) Continuation of application No. PCT/JP2013/002385, filed on Apr. 5, 2013.

(51) Int. Cl.
*A61B 8/08*    (2006.01)
*A61B 5/00*    (2006.01)
(Continued)

(52) U.S. Cl.
CPC .......... *A61B 8/5261* (2013.01); *A61B 5/0035* (2013.01); *A61B 5/0066* (2013.01);
(Continued)

(58) Field of Classification Search
None
See application file for complete search history.

(56) References Cited

U.S. PATENT DOCUMENTS

| | | | | |
|---|---|---|---|---|
| 5,868,666 A | * | 2/1999 | Okada | A61B 1/05 348/76 |
| 2006/0241456 A1 | * | 10/2006 | Karasawa | A61B 8/14 600/447 |

(Continued)

FOREIGN PATENT DOCUMENTS

| | | | | |
|---|---|---|---|---|
| EP | 2540218 A1 | * | 1/2013 | ........... A61B 5/0084 |
| JP | 11-56752 A | | 3/1999 | |

(Continued)

OTHER PUBLICATIONS

English Translation of JP2007313202A (Year: 2007).*

(Continued)

*Primary Examiner* — Bill Thomson
*Assistant Examiner* — Helene Bor
(74) *Attorney, Agent, or Firm* — Buchanan Ingersoll & Rooney PC

(57) ABSTRACT

An imaging apparatus is disclosed for diagnosis generating a first tomographic image and a second tomographic image inside a lumen of a measurement subject body by using an ultrasound signal which is transmitted and received by a first transmitting and receiving unit and an optical signal which is transmitted and received by a second transmitting and receiving unit in a case where a transmitting and receiving unit in which the first transmitting and receiving unit performing transmission and reception of the ultrasound signal and the second transmitting and receiving unit performing transmission and reception of the optical signal are disposed moves in an axial direction while rotating in the lumen of the measurement subject body.

19 Claims, 17 Drawing Sheets

(51) Int. Cl.
*A61B 8/12* (2006.01)
*A61B 8/00* (2006.01)
*A61B 8/14* (2006.01)
*A61B 5/02* (2006.01)

(52) U.S. Cl.
CPC .......... *A61B 5/0084* (2013.01); *A61B 5/6876* (2013.01); *A61B 8/12* (2013.01); *A61B 8/14* (2013.01); *A61B 8/4416* (2013.01); *A61B 5/02007* (2013.01); *A61B 8/5207* (2013.01); *A61B 8/54* (2013.01)

(56) References Cited

U.S. PATENT DOCUMENTS

| | | |
|---|---|---|
| 2011/0237958 A1 | 9/2011 | Onimura |
| 2013/0006105 A1 | 1/2013 | Furuichi |
| 2013/0102865 A1* | 4/2013 | Mandelis ............ A61B 5/0095 600/328 |

FOREIGN PATENT DOCUMENTS

| | | |
|---|---|---|
| JP | 2007-313202 A | 12/2007 |
| JP | 2007313202 A * | 12/2007 |
| JP | 2008-511400 A | 4/2008 |
| JP | 2010-508973 A | 3/2010 |
| JP | 2011-200596 A | 10/2011 |
| JP | 2013-13439 A | 1/2013 |
| WO | WO 2006/028718 A1 | 3/2006 |
| WO | WO 2008/057573 A2 | 5/2008 |

OTHER PUBLICATIONS

International Search Report (PCT/ISA/210) dated May 7, 2013, by the Japanese Patent Office as the International Searching Authority for International Application No. PCT/JP2013/002385.

* cited by examiner

IMAGING APPARATUS FOR DIAGNOSIS AND PROGRAM

CROSS-REFERENCES TO RELATED APPLICATIONS

This application is a continuation of International Application No. PCT/JP2013/002385 filed on Apr. 5, 2013, the entire content of which is incorporated herein by reference.

TECHNICAL FIELD

The present disclosure generally relates to an imaging apparatus for diagnosis, and a program.

BACKGROUND DISCUSSION

Imaging apparatuses for diagnosis have been widely used to perform diagnoses of arteriosclerosis, and to perform preoperative diagnoses or to check postoperative results when intra-vascular treatment is performed using a high-performance catheter such as a balloon catheter, a stent, and the like.

The imaging apparatus for diagnosis can include an ultrasound tomography apparatus for diagnosis (IVUS: intra-vascular ultrasound), and an optical coherent tomography apparatus for diagnosis (OCT: optical coherence tomography), which are different from one another in characteristics.

In addition, recently, an imaging apparatus for diagnosis (an imaging apparatus for diagnosis including an ultrasound transmitting and receiving unit which can transmit and receive ultrasounds, and a light transmitting and receiving unit which can transmit and receive light) in which a function of the IVUS and a function of the OCT are combined together has been proposed (for example, refer to JP-A-11-56752 and JP-T-2010-508973). According to such an imaging apparatus for diagnosis, both a tomographic image (an ultrasound tomographic image) utilizing the characteristics of the IVUS which can measure a high depth region, and a tomographic image (an optical coherent tomographic image, hereinafter, referred to as "an optical tomographic image") utilizing the characteristics of the OCT which can perform measurement at a high resolution, by performing scanning once can be generated.

SUMMARY

When transmitting and receiving light with the light transmitting and receiving unit, there is a need to perform flushing for replacing blood flow in a blood vessel by using a flushing liquid. Therefore, in a case of an imaging apparatus for diagnosis in which a function of IVUS and a function of OCT are combined together, ultrasounds are transmitted into blood when utilizing only the function of the IVUS, whereas ultrasounds are transmitted to the flushing liquid when utilizing both the function of the IVUS and the function of the OCT.

Since the flushing liquid has a higher attenuation factor of ultrasounds compared to blood, when utilizing the function of the IVUS in a state where blood is flushed, the signal strength of ultrasounds received by an ultrasound transmitting and receiving unit can be degraded. In addition, there are various types of flushing liquids in a flushing liquid utilized in flushing, and the attenuation factor of ultrasounds differs depending on the type of the flushing liquid.

In this manner, in a case of the imaging apparatus for diagnosis in which the function of the IVUS and the function of the OCT are combined together, generated ultrasound tomographic images for the same blood vessel look different from each other depending on the conditions when transmitting and receiving ultrasounds. For such a reason, when generating homogenous ultrasound tomographic images with the imaging apparatus for diagnosis in which the function of the IVUS and the function of the OCT are combined together, it is important to consider the conditions affecting the characteristics of the ultrasound transmitting and receiving unit.

An imaging apparatus for diagnosis is disclosed, which includes a plurality of transmitting and receiving units, in which homogenous tomographic images are generated.

An imaging apparatus is disclosed for diagnosis generating a first tomographic image and a second tomographic image inside a lumen of a measurement subject body by using an ultrasound signal which is transmitted and received by a first transmitting and receiving unit and an optical signal which is transmitted and received by a second transmitting and receiving unit in a case where a transmitting and receiving unit in which the first transmitting and receiving unit performing transmission and reception of the ultrasound signal and the second transmitting and receiving unit performing transmission and reception of the optical signal are disposed moves in an axial direction while rotating in the lumen of the measurement subject body, the apparatus including first discrimination means for discriminating whether to generate both the first tomographic image and the second tomographic image or to generate only the first tomographic image; and gain correction means for changing a gain at the time of generating the first tomographic image based on the ultrasound signal received by the first transmitting and receiving unit, in accordance with a result of discrimination made by the first discrimination means.

A method is disclosed of controlling an imaging apparatus for diagnosis generating a first tomographic image and a second tomographic image inside a lumen of a measurement subject body by using an ultrasound signal which is transmitted and received by a first transmitting and receiving unit and an optical signal which is transmitted and received by a second transmitting and receiving unit in a case where a transmitting and receiving unit in which the first transmitting and receiving unit performing transmission and reception of the ultrasound signal and the second transmitting and receiving unit performing transmission and reception of the optical signal are disposed moves in an axial direction while rotating in the lumen of the measurement subject body, the method comprising: discriminating whether to generate both the first tomographic image and the second tomographic image or to generate only the first tomographic image; and changing a gain at a time of generating the first tomographic image based on the ultrasound signal received by the first transmitting and receiving unit.

According to the present disclosure, homogenous tomographic images in an imaging apparatus for diagnosis having a plurality of transmitting and receiving units can be generated.

Other features and advantages of the present disclosure will be clearly described below with reference to the accompanying drawings. In the accompanying drawings, the same reference numerals and signs will be applied to the same or similar constitutions.

BRIEF DESCRIPTION OF THE DRAWINGS

The accompanying drawings are incorporated in this Description, take part in the constitution, illustrate embodiments of the present disclosure, and are used to describe the principle of the present disclosure together with the disclosure thereof.

DETAILED DESCRIPTION

Hereinafter, each embodiment of the present disclosure will be described in detail with reference to the accompanying drawings as necessary. The embodiments described below are preferable specification examples of the present disclosure and are subjected to various limitations, which are technically preferable. However, the scope of the present disclosure is not limited to those aspects unless otherwise specified so as to particularly limit the present disclosure in the following description.

1. Constitution of Appearance of Imaging Apparatus for Diagnosis

Figure 1:
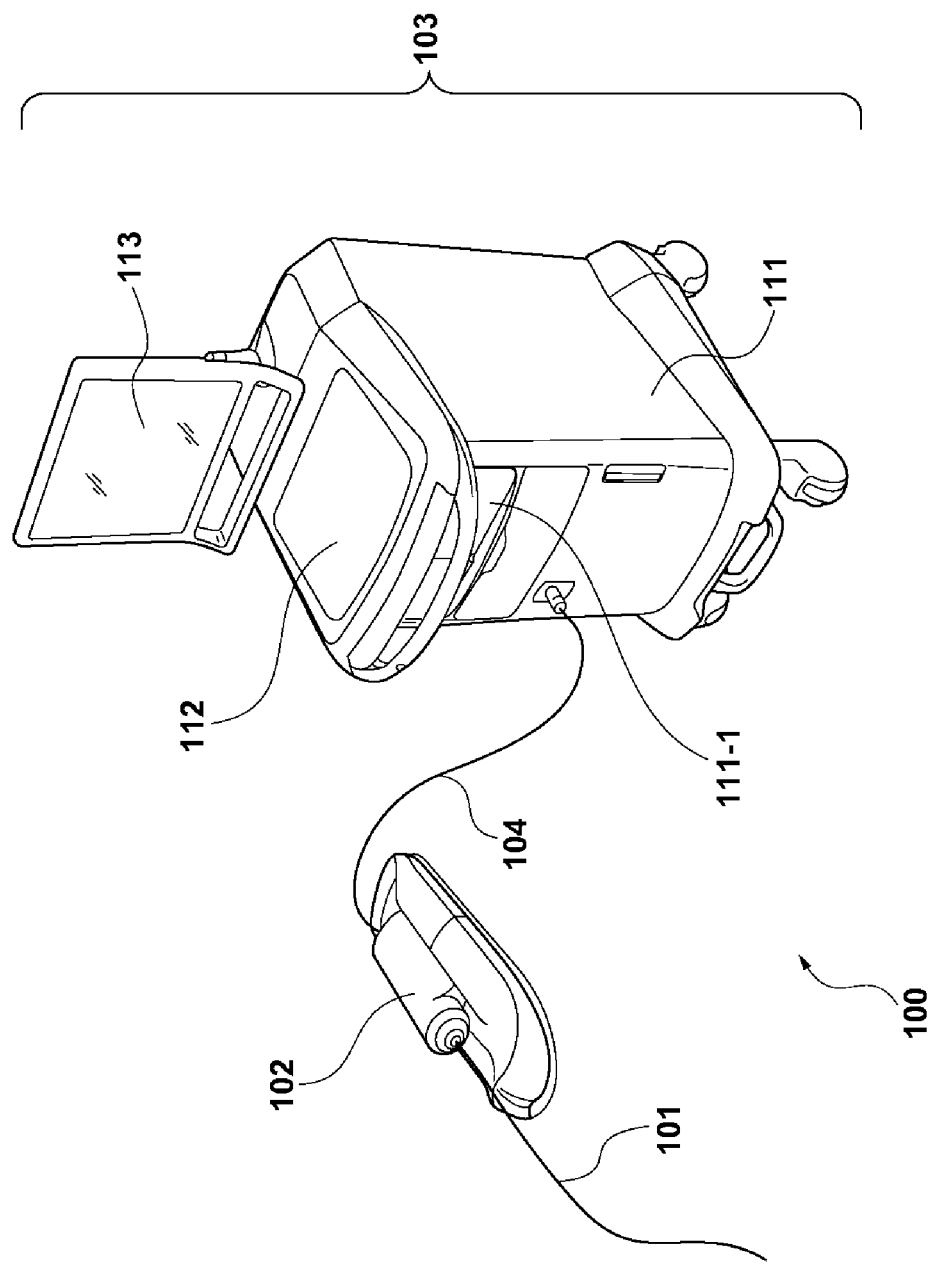
FIG. 1 is a diagram illustrating a constitution of the appearance of an imaging apparatus for diagnosis according to an exemplary embodiment of the present disclosure.

FIG. 1 is a diagram illustrating a constitution of the appearance of an imaging apparatus 100 for diagnosis (an imaging apparatus for diagnosis including a function of IVUS and a function of OCT) according to an embodiment of the present disclosure.

As illustrated in FIG. 1, the imaging apparatus 100 for diagnosis can include a probe unit 101, a scanner and pull-back unit 102 and an operation control device 103. The scanner and pull-back unit 102 and the operation control device 103 are connected to each other through a signal wire 104 so as to be able to transfer various signals.

An imaging core which is directly inserted into a blood vessel (a measurement subject body) is interpolated into the probe unit 101. The imaging core can include an ultrasound transmitting and receiving unit which transmits ultrasounds based on a pulse signal into a blood vessel and receives reflected waves from the inside of the blood vessel, and a light transmitting and receiving unit which continuously transmits transferred light (measurement light) into a blood vessel and continuously receives reflected light from the inside of the blood vessel. In the imaging apparatus 100 for diagnosis, the imaging core is used to measure a state inside a blood vessel.

The probe unit 101 is attached to the scanner and pull-back unit 102 in a freely detachable manner. A built-in motor is driven so as to define axial motion inside a blood vessel and rotary motion around the axis of the imaging core which is interpolated into the probe unit 101. In addition, the scanner and pull-back unit 102 acquires reflected waves received by the ultrasound transmitting and receiving unit and the reflected light received by the light transmitting and receiving unit, thereby performing transmission to the operation control device 103.

The operation control device 103 can include a function of inputting various setting values when performing measurement and a function of processing data obtained through the measurement and displaying a tomographic image of the inside of a blood vessel.

In the operation control device 103, the reference numeral 111 indicates a main body control unit, which generates ultrasound data based on reflected waves obtained through the measurement, and performs processing of ultrasound line data generated based on the ultrasound data, thereby generating an ultrasound tomographic image. Moreover, reflected light obtained through the measurement is caused to interfere with reference light obtained by separating light from a light source, thereby generating interference light data, and processing of optical line data generated based on the interference light data is performed, thereby generating an optical tomographic image.

The reference numeral 111-1 indicates a printer and DVD recorder, which prints a processing result of the main body control unit 111 and stores the processing result as data. The reference numeral 112 indicates an operation panel, and a user inputs various setting values and instructions via the operation panel 112. The reference numeral 113 indicates an LCD monitor as a display device, which displays a tomographic image generated in the main body control unit 111.

Figure 2:
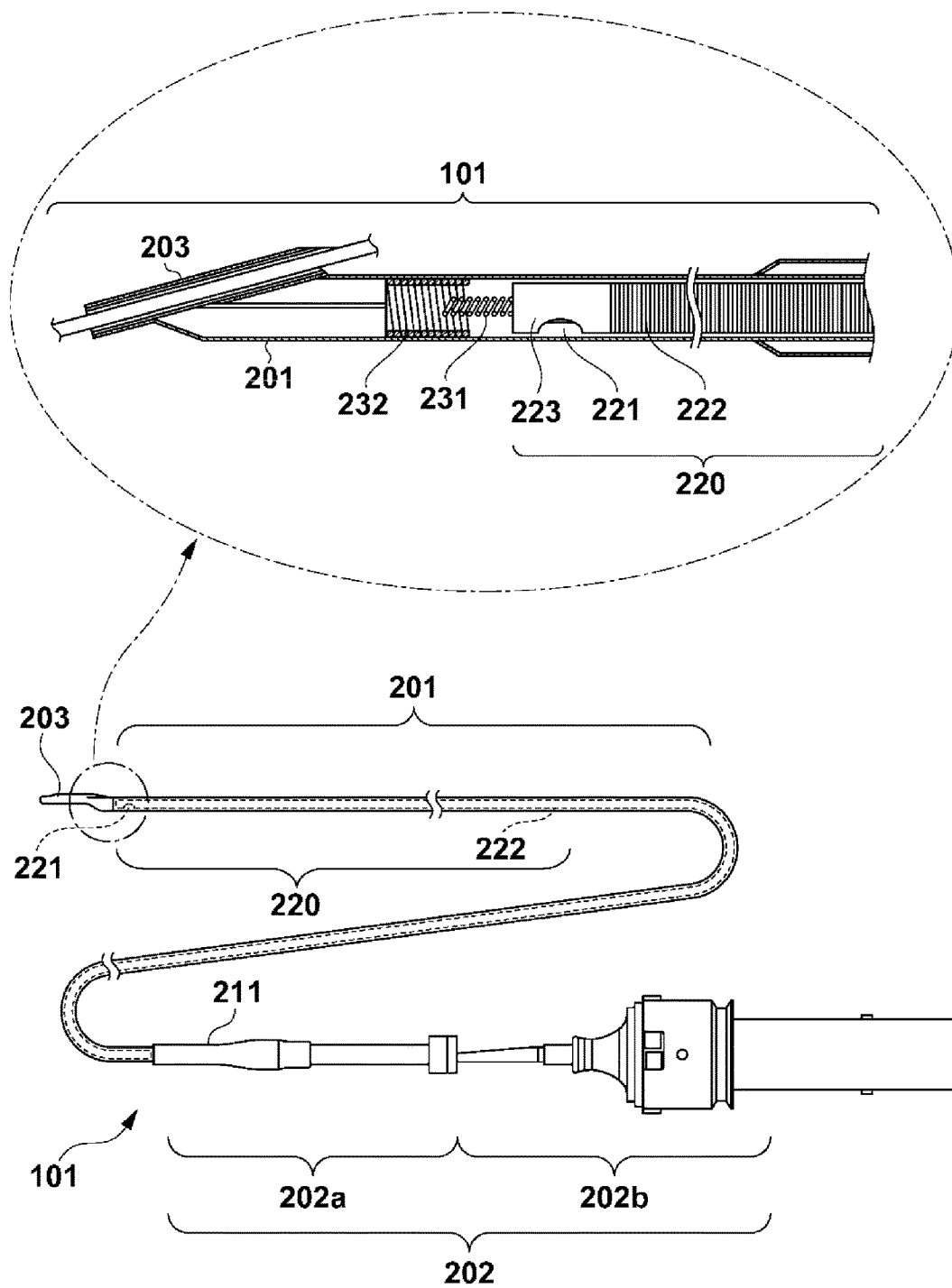
FIG. 2 is a diagram illustrating an overall constitution of a probe unit and a cross-sectional constitution of a distal end portion.

2. Overall Constitution of Probe Unit and Cross-sectional Constitution of Distal End Portion Subsequently, an overall constitution of the probe unit 101 and a cross-sectional constitution of a distal end portion will be described with reference to FIG. 2. As illustrated in FIG. 2, the probe unit 101 is constituted to include an elongated catheter sheath 201 which is inserted into a blood vessel, and a connector portion 202, which is disposed on a hand side of a user to be operated by the user without being inserted into a blood vessel. A guide wire lumen tube 203 for constituting a guide wire lumen is provided at the distal end of the catheter sheath 201. The catheter sheath 201 forms a lumen which continues from a portion connected to the guide wire lumen tube 203 to a portion connected to the connector portion 202.

Inside the lumen of the catheter sheath 201, an imaging core 220 including a transmitting and receiving unit 221 and a coiled drive shaft 222 is inserted through the catheter sheath 201 throughout substantially the overall length of the catheter sheath 201. In the transmitting and receiving unit 221, the ultrasound transmitting and receiving unit for transmitting and receiving ultrasounds and the light transmitting and receiving unit for transmitting and receiving light are disposed. The drive shaft 222 is internally provided with an electric signal cable and an optical fiber cable and transfers a rotary drive force for rotating them.

The connector portion 202 can include a sheath connector 202a which is constituted to be unified to a proximal end of the catheter sheath 201, and a drive shaft connector 202b which is constituted to rotatably fix the drive shaft 222 to a proximal end of the drive shaft 222.

A kink-proof protector 211 is provided at a boundary portion between the sheath connector 202a and the catheter sheath 201. Accordingly, predetermined rigidity is maintained so as to be able to prevent bending (kinking) occurring due to a rapid change of properties.

The proximal end of the drive shaft connector 202b is attached to the scanner and pull-back unit 102 in a freely detachable manner.

Subsequently, a cross-sectional constitution of the distal end portion of the probe unit 101 will be described. Inside the lumen of the catheter sheath 201, the imaging core 220 including a housing 223 and the drive shaft 222 is inserted throughout substantially the overall length of the catheter sheath 201, thereby forming the probe unit 101. In the housing 223, there is provided the transmitting and receiving unit 221 in which the ultrasound transmitting and receiving unit for transmitting and receiving ultrasounds and the light transmitting and receiving unit for transmitting and receiving light are disposed. The drive shaft 222 transfers a rotary drive force for rotating the housing 223.

The drive shaft 222 can cause the transmitting and receiving unit 221 to perform the rotary motion and the axial motion with respect to the catheter sheath 201. The drive shaft 222 is constituted of a multiplex-multilayer bonding coil formed with a metal wire, for example, stainless steel having characteristics of being soft and favorably transferring rotations. Then, the electric signal cable and the optical fiber cable (the single mode optical fiber cable) are arranged inside of the drive shaft 222.

The housing 223 can be a metallic pipe having a short cylindrical shape in which a notch portion is partially provided. The housing 223 can be molded by performing carving from a metal ingot and metal powder injection molding (MIM). In addition, a short coiled elastic member 231 is provided on the distal end side of the housing 223.

The elastic member 231 can be formed with a coiled stainless steel wire. Since the elastic member 231 is disposed on the distal end side, the imaging core 220 can be prevented from being caught inside the catheter sheath 201 when moving forward and rearward.

The reference numeral 232 indicates a reinforcement coil which is provided for the purpose of preventing sudden bending at the distal end portion of the catheter sheath 201.

The guide wire lumen tube 203 has a lumen for guide wire allowing a guide wire to be inserted. The guide wire lumen tube 203 is used for receiving the guide wire which has been inserted into a blood vessel in advance, and causing the guide wire to guide the catheter sheath 201 to a target lesion.

3. Cross-sectional Constitution of Imaging Core

Figure 3:
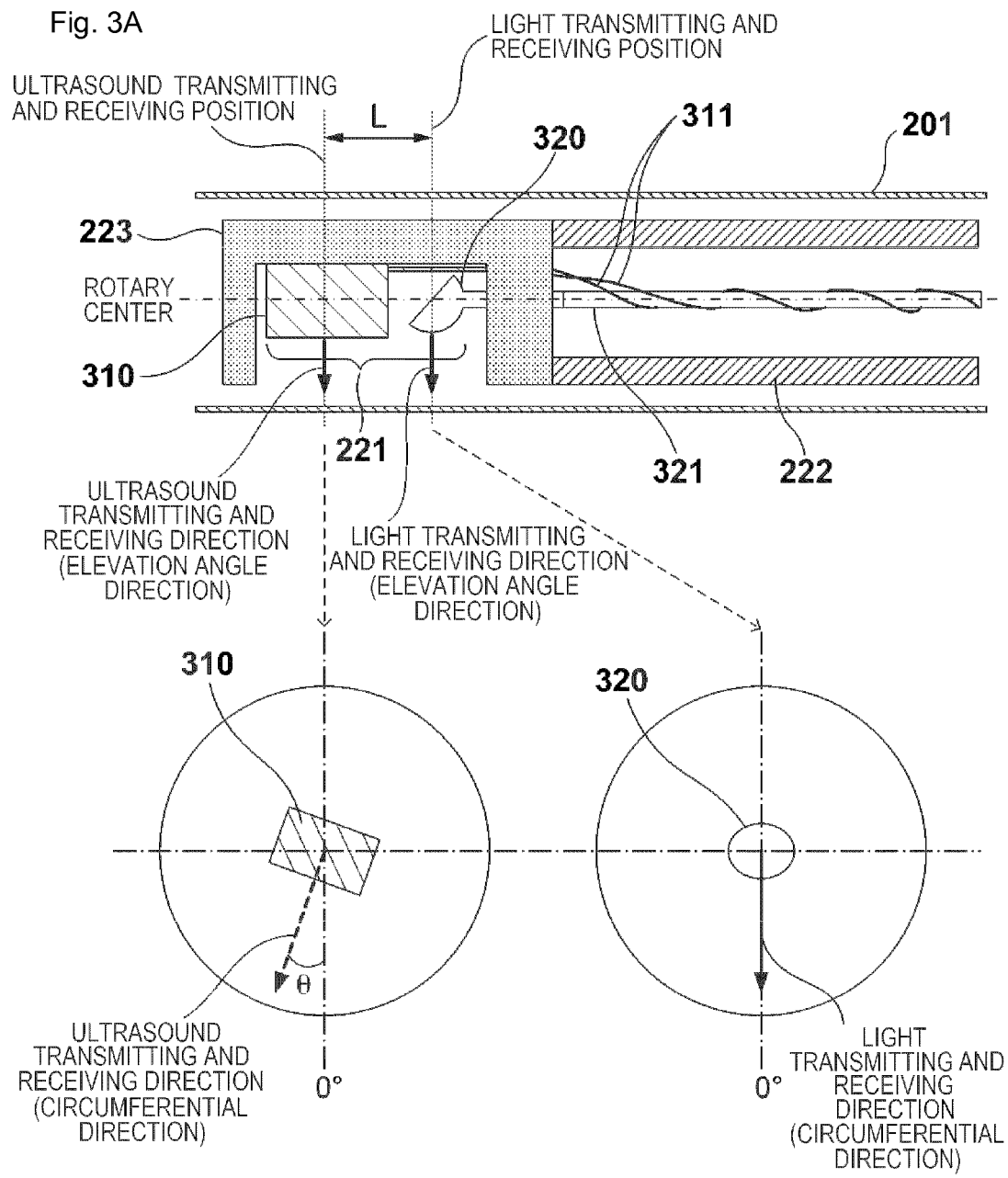
FIG. 3A is a diagram illustrating a cross-sectional constitution of an imaging core, and a disposition of an ultrasound transmitting and receiving unit and a light transmitting and receiving unit.
FIG. 3B is a cross-sectional view when being cut on a plane, which is substantially orthogonal to the rotary center axis at an ultrasound transmitting and receiving position.
FIG. 3C is a cross-sectional view when being cut on a plane, which is substantially orthogonal to the rotary center axis at the light transmitting and receiving position.

Subsequently, a cross-sectional constitution of the imaging core 220 and a disposition of the ultrasound transmitting and receiving unit and the light transmitting and receiving unit will be described. FIG. 3A is a diagram illustrating the cross-sectional constitution of the imaging core and the disposition of the ultrasound transmitting and receiving unit and the light transmitting and receiving unit.

As illustrated in FIG. 3A, the transmitting and receiving unit 221 which is arranged inside the housing 223 can include an ultrasound transmitting and receiving unit 310 and a light transmitting and receiving unit 320. The ultrasound transmitting and receiving unit 310 and the light transmitting and receiving unit 320 are disposed on a rotary center axis (on a dot and dash line in FIG. 3a) of the drive shaft 222 along the axial direction while being separated from each other by a distance L.

Among them, the ultrasound transmitting and receiving unit 310 is disposed on the distal end side of the probe unit 101, and the light transmitting and receiving unit 320 is disposed on the proximal end side of the probe unit 101.

The ultrasound transmitting and receiving unit 310 and the light transmitting and receiving unit 320 are attached to the inside of the housing 223 so as to cause each of an ultrasound transmitting and receiving direction (an elevation angle direction) of the ultrasound transmitting and receiving unit 310 and a light transmitting and receiving direction (an elevation angle direction) of the light transmitting and receiving unit 320 to be substantially 90° with respect to the axial direction of the drive shaft 222. It can be desirable to perform attachment while causing each of the transmitting and receiving directions to be slightly misaligned from 90° so as not to receive reflection from the inner surface of the lumen in the catheter sheath 201.

Inside the drive shaft 222, an electrical signal cable 311 which is connected to the ultrasound transmitting and receiving unit 310, and an optical fiber cable 321 which is connected to the light transmitting and receiving unit 320 are disposed. The electrical signal cable 311 is wound around the optical fiber cable 321 in a spiral manner.

FIG. 3B is a cross-sectional view when being cut on a plane which is substantially orthogonal to the rotary center axis at an ultrasound transmitting and receiving position. As illustrated in FIG. 3B, when the downward direction of the sheet is considered as zero degrees, the ultrasound transmitting and receiving direction (the circumferential direction (also referred to as the azimuth angle direction)) of the ultrasound transmitting and receiving unit 310 becomes 8 degrees.

FIG. 3C is a cross-sectional view when being cut on a plane which is substantially orthogonal to the rotary center axis at the light transmitting and receiving position. As illustrated in FIG. 3C, when the downward direction of the sheet is considered as zero degrees, the light transmitting and receiving direction (the circumferential direction) of the light transmitting and receiving unit 320 becomes zero degrees. In accordance with an exemplary embodiment, for example, the ultrasound transmitting and receiving unit 310 and the light transmitting and receiving unit 320 are disposed so as to cause the ultrasound transmitting and receiving direction (the circumferential direction) of the ultrasound transmitting and receiving unit 310 and the light transmitting and receiving direction (the circumferential direction) of the light transmitting and receiving unit 320 to be mutually misaligned by an angular difference of 8 degrees.

4. Functional Constitution of Imaging Apparatus for Diagnosis

Figure 4:
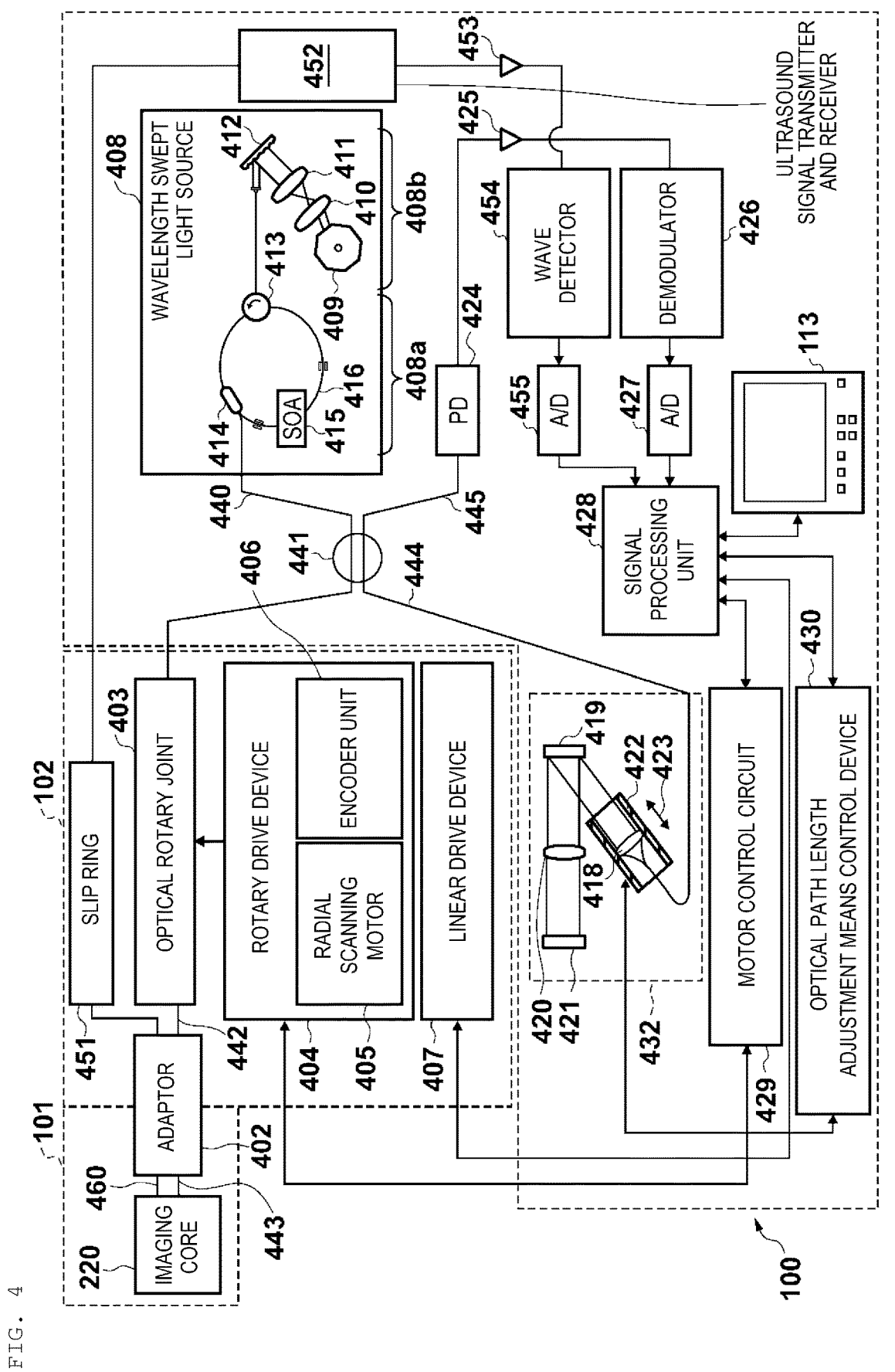
FIG. 4 is a diagram illustrating a functional constitution of the imaging apparatus for diagnosis.

A functional constitution of the imaging apparatus 100 for diagnosis will be described. FIG. 4 is a diagram illustrating the functional constitution of the imaging apparatus 100 for diagnosis in which the function of the IVUS and the function of the OCT (herein, a swept source OCT as an example) are combined together. An imaging apparatus for diagnosis in which the function of the IVUS and a function of different OCT are combined together also has a similar functional constitution, thereby omitting the description thereof herein.

(1) Function of IVUS

The imaging core 220 internally includes the ultrasound transmitting and receiving unit 310 at the distal end of the imaging core 220. The ultrasound transmitting and receiving unit 310 transmits ultrasounds to a biological tissue in a blood vessel based on pulse waves transmitted from an ultrasound signal transmitter and receiver 452, and receives reflected waves (echo) thereof, thereby transmitting the reflected waves as an ultrasound signal to the ultrasound signal transmitter and receiver 452 via an adaptor 402 and a slip ring 451.

In the scanner and pull-back unit 102, a rotary drive portion side of the slip ring 451 is rotatively driven by a radial scanning motor 405 of a rotary drive device 404. In addition, a rotary angle of the radial scanning motor 405 is detected by an encoder unit 406. Moreover, the scanner and pull-back unit 102 can include a linear drive device 407 and defines the axial motion of the imaging core 220 based on a signal from a signal processing unit 428.

The ultrasound signal transmitter and receiver 452 can include a transmission wave circuit and a reception wave circuit (not illustrated). The transmission wave circuit transmits pulse waves to the ultrasound transmitting and receiving unit 310 inside the imaging core 220 based on a control signal transmitted from the signal processing unit 428.

In addition, the reception wave circuit receives an ultrasound signal from the ultrasound transmitting and receiving unit 310 inside the imaging core 220. The received ultrasound signal is amplified by an amplifier 453, and then, the amplified signal is input to a wave detector 454 so as to be subjected to wave detection.

Moreover, in an A/D converter 455, an ultrasound signal output from the wave detector 454 can be sampled at, for example, 30.6 MHz at as many as 200 points, thereby generating digital data (ultrasound line data) for one line. Herein, the frequency is set to, for example, 30.6 MHz on the premise that the sampling is performed at 200 points with respect to the depth of, for example, 5 mm when the sound velocity is considered to be, for example, 1,530 m/sec. Therefore, the sampling frequency is not particularly limited thereto.

The ultrasound line data generated by the A/D converter 455 in a line unit is input to the signal processing unit 428. In the signal processing unit 428, the ultrasound line data is converted into a gray scale so as to generate an ultrasound tomographic image at each of the positions in a blood vessel, thereby outputting the ultrasound tomographic image to the LCD monitor 113 at a predetermined frame rate.

The signal processing unit 428 is connected to a motor control circuit 429 and receives a video synchronization signal of the motor control circuit 429. In the signal processing unit 428, the ultrasound tomographic image is generated by being synchronized with the received video synchronization signal.

In addition, the video synchronization signal of the motor control circuit 429 is also transmitted to the rotary drive device 404, and the rotary drive device 404 outputs a drive signal which is synchronized with the video synchronization signal.

(2) Function of Swept Source OCT

Subsequently, a functional constitution of the swept source OCT will be described with reference to the same diagram. The reference numeral 408 indicates a wavelength swept light source (swept laser), which is a type of an extended-cavity laser constituted of an optical fiber 416 coupled with a semiconductor optical amplifier 415 (SOA) in a ring shape, and a polygon scanning filter (408b).

Light output from the SOA 415 passes through the optical fiber 416 and enters the polygon scanning filter 408b. The light is subjected to wavelength selection herein, is amplified by the SOA 415, and is lastly output from a coupler 414.

In the polygon scanning filter 408b, the wavelength is selected through a combination of a diffraction grating 412 which diffracts light, and a polygon mirror 409. In accordance with an exemplary embodiment, for example, the light diffracted by the diffraction grating 412 is concentrated on a surface of the polygon mirror 409 by using two lenses (410 and 411). Accordingly, only the light having a wavelength orthogonal to the polygon mirror 409 returns to the same optical path, thereby being output from the polygon scanning filter 408b. For example, time sweeping of a wavelength can be performed by rotating the polygon mirror 409.

In the polygon mirror 409, for example, a 32-hedron mirror can be used and the number of rotations is approximately 50,000 rpm. In accordance with an exemplary embodiment, for example, a high-speed and high-output wavelength sweeping through the wavelength swept source method in which the polygon mirror 409 and the diffraction grating 412 are combined together can be performed.

Light of the wavelength swept light source 408 output from the coupler 414 is incident on one end of a first single mode fiber 440, thereby being transferred to the distal end side thereof. The first single mode fiber 440 is optically coupled to a second single mode fiber 445 and a third single mode fiber 444 in a photo coupler unit 441 in the middle therebetween.

On the distal end side from the photo coupler unit 441 of the first single mode fiber 440, an optical rotary joint (an optical coupling portion) 403 which connects a non-rotary portion (fixed portion) and a rotary portion (rotary drive portion) with each other and transfers light is provided inside the rotary drive device 404.

Moreover, on a distal end side of a fourth single mode fiber 442 in the optical rotary joint (the optical coupling portion) 403, a fifth single mode fiber 443 of the probe unit 101 is connected thereto via the adaptor 402 in a freely detachable manner. Accordingly, light from the wavelength swept light source 408 is transferred to the rotatably driven fifth single mode fiber 443 which is inserted through the inside of the imaging core 220.

Irradiation of the transferred light in rotary motion and axial motion is performed with respect to a biological tissue in a blood vessel from the light transmitting and receiving unit 320 of the imaging core 220. A portion of the reflected light scattering on a surface or inside a biological tissue is collected by the light transmitting and receiving unit 320 of the imaging core 220, and returns to the first single mode fiber 440 side via the optical path in reverse. Moreover, the portion of the reflected light moves to the second single mode fiber 445 side by the photo coupler unit 441 and is emitted from one end of the second single mode fiber 445. Thereafter, the portion of the reflected light is received by a photo detector (for example, a photo diode 424).

The rotary drive portion side of the optical rotary joint 403 is rotatively driven by the radial scanning motor 405 of the rotary drive device 404.

Meanwhile, an optical path length variable mechanism 432 for performing fine adjustment of the length of the optical path of the reference light is provided at the distal end on a side opposite to the photo coupler unit 441 of the third single mode fiber 444.

The optical path length variable mechanism 432 can include an optical path length changing means for changing the length of the optical path corresponding to a fluctuation in the length of each probe unit 101 so as to be able to absorb the fluctuation in the length thereof when the probe unit 101 is replaced and used.

The third single mode fiber 444 and a collimating lens 418 are provided on a one-axis stage 422 which is movable in the optical-axis direction thereof as indicated by the arrow 423, thereby forming the optical path length changing means.

In accordance with an exemplary embodiment, for example, the one-axis stage 422 functions as the optical path length changing means having a variable range of the optical path length as wide as the fluctuation in the length of the optical path of the probe unit 101 can be absorbed when the probe unit 101 is replaced. Moreover, the one-axis stage 422 can also include an adjustment means for adjusting an offset. For example, even when the distal end of the probe unit 101 is not in close contact with a surface of a biological tissue, a state of interfering can be set with the reflected light from the surface position of the biological tissue by performing fine changing of the length of the optical path through the one-axis stage.

The light whose length of the optical path is subjected to fine adjustment through the one-axis stage 422, and which is reflected by the mirror 421 via a grating 419 and a lens 420 is mixed with light obtained from the first single mode fiber 440 side in the photo coupler unit 441 which is provided in the middle of the third single mode fiber 444, thereby being received by the photo diode 424.

The interference light received by the photo diode 424 as described above is subjected to photoelectric conversion, thereby being input to a demodulator 426 after being amplified by the amplifier 425. The demodulator 426 performs demodulation processing of extracting only a signal portion of the interference light, and an output thereof is input to an A/D converter 427 as an interference light signal.

In the A/D converter 427, the interference light signal can be sampled, for example, at 180 MHz at as many as 2,048 points, for example, thereby generating digital data (interference light data) for one line. The sampling frequency can be set to, for example, 180 MHz on the premise that approximately 90% of a periodical cycle (12.5 μsec) of the wavelength sweeping is extracted as digital data at 2,048 points when a repetition frequency of the wavelength sweeping is set to, for example, 80 kHz. However, the sampling frequency is not particularly limited thereto.

The interference light data generated by the A/D converter 427 in a line unit is input to the signal processing unit 428. The signal processing unit 428 generates data (the optical line data) in a depth direction by causing the interference light data to be subjected to frequency resolution through fast fourier transform (FFT). Then, the generated data is subjected to coordinate conversion so as to construct an optical tomographic image at each position in a blood vessel, thereby outputting the constructed image to the LCD monitor 113 at a predetermined frame rate.

Furthermore, the signal processing unit 428 is further connected to an optical path length adjustment means control device 430. In addition, the signal processing unit 428 controls a position of the one-axis stage 422 via the optical path length adjustment means control device 430.

5. Description of Signal Processing Unit 428

Figure 5:
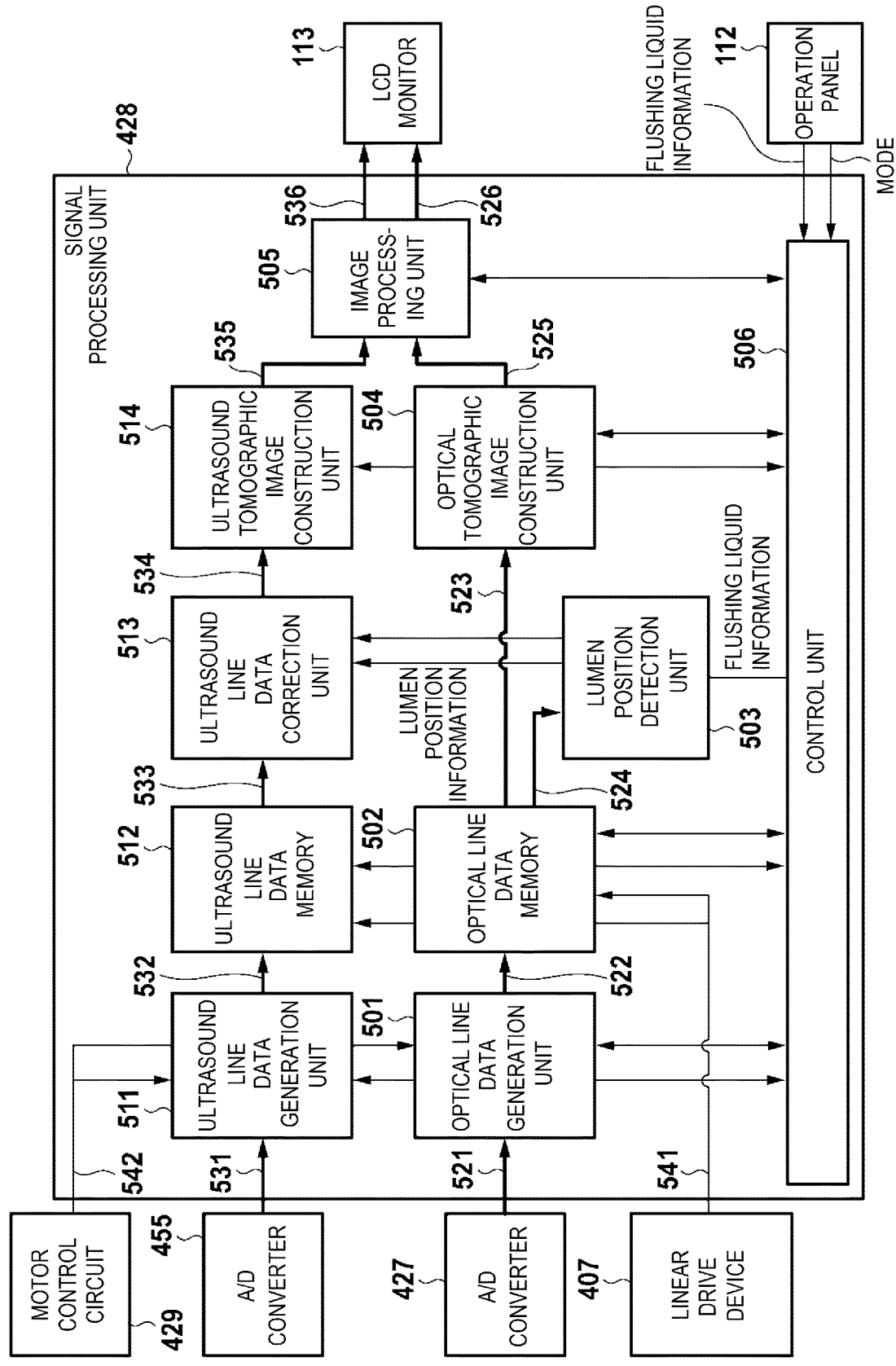
FIG. 5 is a diagram illustrating a functional constitution of a signal processing unit of the imaging apparatus for diagnosis.

Subsequently, a functional constitution of the signal processing unit 428 of the imaging apparatus 100 for diagnosis will be described. FIG. 5 is a diagram illustrating a functional constitution of the signal processing unit 428 of the imaging apparatus 100 for diagnosis and related functional blocks thereof. The functional constitution illustrated in FIG. 5 may be realized by using exclusive hardware or may be partially realized through software (for example, by causing a computer to execute a program for realizing the function).

As illustrated in FIG. 5, the interference light data 521 generated by the A/D converter 427 is processed so as to have 512 lines per one rotation in an optical line data generation unit 501 inside the signal processing unit 428, by using a signal of the encoder unit 406 of the radial scanning motor 405 output from the motor control circuit 429.

Optical line data 522 output by the optical line data generation unit 501 is stored in an optical line data memory 502 by the volume for each rotation (one frame) based on an instruction from a control unit 506. In this case, the control unit 506 counts pulse signals 541, which are output by a movement amount detector of the linear drive device 407. When storing the optical line data 522 in the optical line data memory 502, each of the counted values at the time of generating the optical line data 522 is caused to correspond thereto.

Optical line data 523 which is stored so as to correspond to the counted value is input to an optical tomographic image construction unit 504 and is subjected to Rθ conversion after various types of processing (line addition averaging processing, filtering processing, and the like) are performed, thereby being sequentially output as optical tomographic images 525.

In addition, optical line data 524 stored so as to correspond thereto as the counted value is also input to a lumen position detection unit 503, and a position of the lumen is detected regarding each item of the optical line data in the lumen position detection unit 503, thereby being input to an ultrasound line data correction unit 513 as lumen position information.

An optical tomographic image 525 output from the optical tomographic image construction unit 504 is subjected to image processing by an image processing unit 505 so as to be displayed on the LCD monitor 113, and then, is output to the LCD monitor 113 as an optical tomographic image 526.

Similarly, ultrasound data 531 generated by the A/D converter 455 is processed so as to have 512 lines per one rotation in an ultrasound line data generation unit 511 inside the signal processing unit 428, using a signal of the encoder unit 406 of the radial scanning motor 405, which is output from the motor control circuit 429.

Ultrasound line data 532 output by the ultrasound line data generation unit 511 is stored in an ultrasound line data memory 512 by the volume for each rotation (one frame) based on an instruction from the control unit 506. In this case, the control unit 506 counts pulse signals 541, which are output by the movement amount detector of the linear drive device 407. When storing the ultrasound line data 532 in the line data memory 512, each of the counted values at the time of generating the ultrasound line data 532 is caused to correspond thereto (the corresponding counted values at this time are the counted values in which the above-described angular difference θ and the distance L are considered. For example, if the count values are the same, the ultrasound line data and the optical line data can be considered to be indicating the same position in a blood vessel.

Ultrasound line data 533 which is stored so as to correspond to the counted value is input to the ultrasound line data correction unit 513, and gain correction is executed based on information received by the control unit 506 related to a flushing liquid. The flushing liquid can be a liquid used when performing a flushing operation. The gains can be stored in the control unit 506 as information related to the flushing liquid by being classified for each type of the flushing liquid in advance. The gains for blood are also stored together as the default thereof. When the lumen position information is received by the lumen position detection unit 503, gain correction is executed regarding the ultrasound line data corresponding to an outer side from the position of the lumen which is specified by the lumen position information (will be described later in detail).

The flushing liquid information is input by a user via the operation panel 112. In addition, in the operation panel 112, when generating a tomographic image, any mode between a dual mode for generating both the ultrasound tomographic image and the optical tomographic image, and a single mode for generating any one of the ultrasound tomographic image and the optical tomographic image is input.

Ultrasound line data 534 which is subjected to gain correction performed by the ultrasound line data correction unit 513 is input to an ultrasound tomographic image construction unit 514. Then, the ultrasound line data 534 is subjected to Re conversion after various types of processing (line addition averaging processing, filtering processing, and the like) are performed by the ultrasound tomographic image construction unit 514 based on an instruction from the control unit 506, thereby being sequentially output as ultrasound tomographic images 535.

Moreover, the ultrasound tomographic image 535 is subjected to image processing by the image processing unit 505 so as to be displayed on the LCD monitor 113, and then, is output to the LCD monitor 113 as an ultrasound tomographic image 536.

6. Operation of Imaging Core 220

Subsequently, a relationship between an operation of the imaging core 220 in a blood vessel and line data (the ultrasound line data and the optical line data) acquired by the operation of the imaging core 220 will be described.

Figure 6:
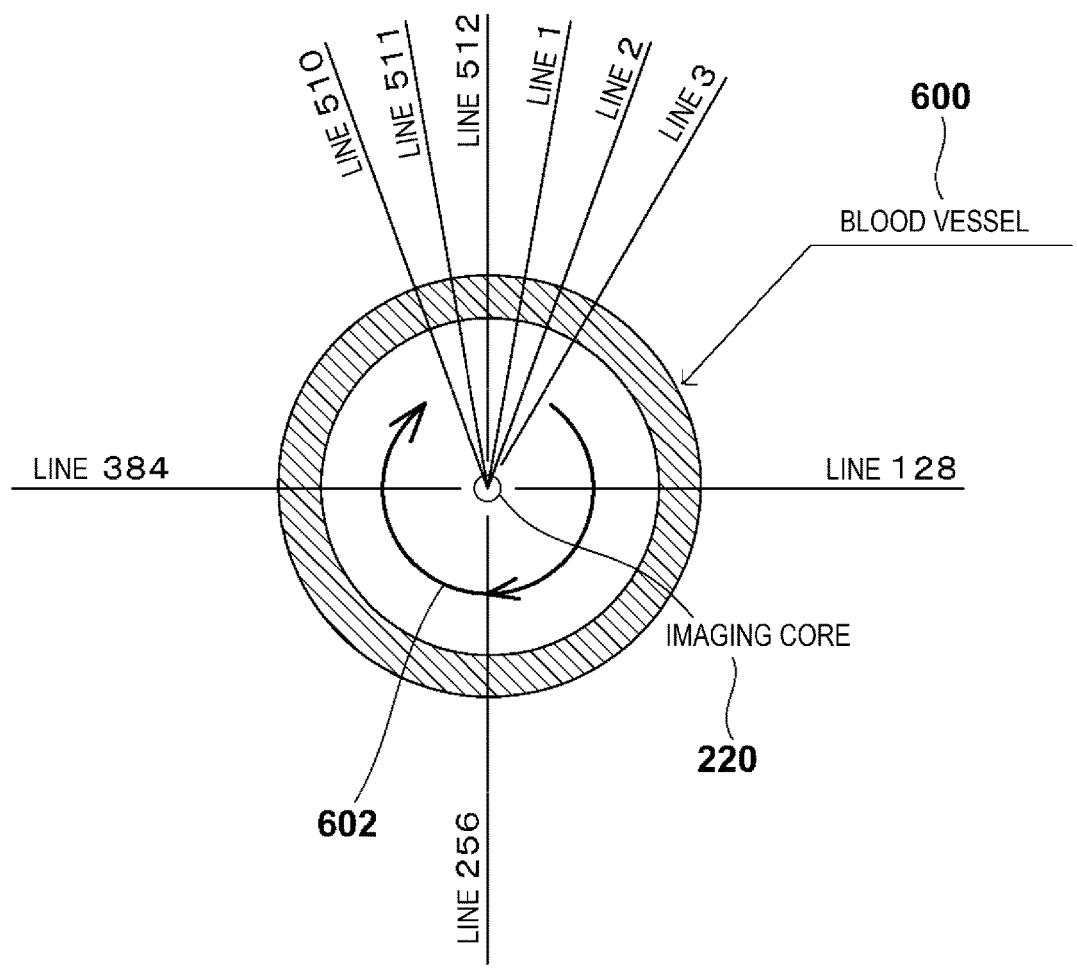
FIG. 6 is a diagram illustrating a data structure of a generated tomographic image.

FIG. 6 illustrates a state where the imaging core 220 inserted through the inside of a blood vessel 600 is seen in a cross-sectional direction of the blood vessel 600. When processing of generating a tomographic image starts in the above-described state, the radial scanning motor 405 rotates the imaging core 220 in a direction of an arrow 602.

In this case, in the ultrasound transmitting and receiving unit 310, transmission/reception of ultrasounds is performed at each of the rotary angles. The lines 1, 2, and so on to 512 indicate transmitting and receiving directions of ultrasounds at each of the rotary angles. In the imaging apparatus 100 for diagnosis according to the present embodiment, while the ultrasound transmitting and receiving unit 310 turns 360 degrees in the blood vessel 600, transmission/reception of ultrasounds is intermittently performed 512 times. Accordingly, 512 items of the ultrasound line data can be generated.

Similarly, in the light transmitting and receiving unit 320 as well, transmission/reception of light is performed at each of the rotary angles. While the light transmitting and receiving unit 320 turns 360 degrees in the blood vessel 600, transmission/reception of light is continuously performed 512 times. Accordingly, 512 items of the optical line data are generated.

7. Description of Each Line Data

Subsequently, the ultrasound line data and the optical line data which are respectively stored in the ultrasound line data memory 512 and the optical line data memory 502 will be described.

Figure 7A:
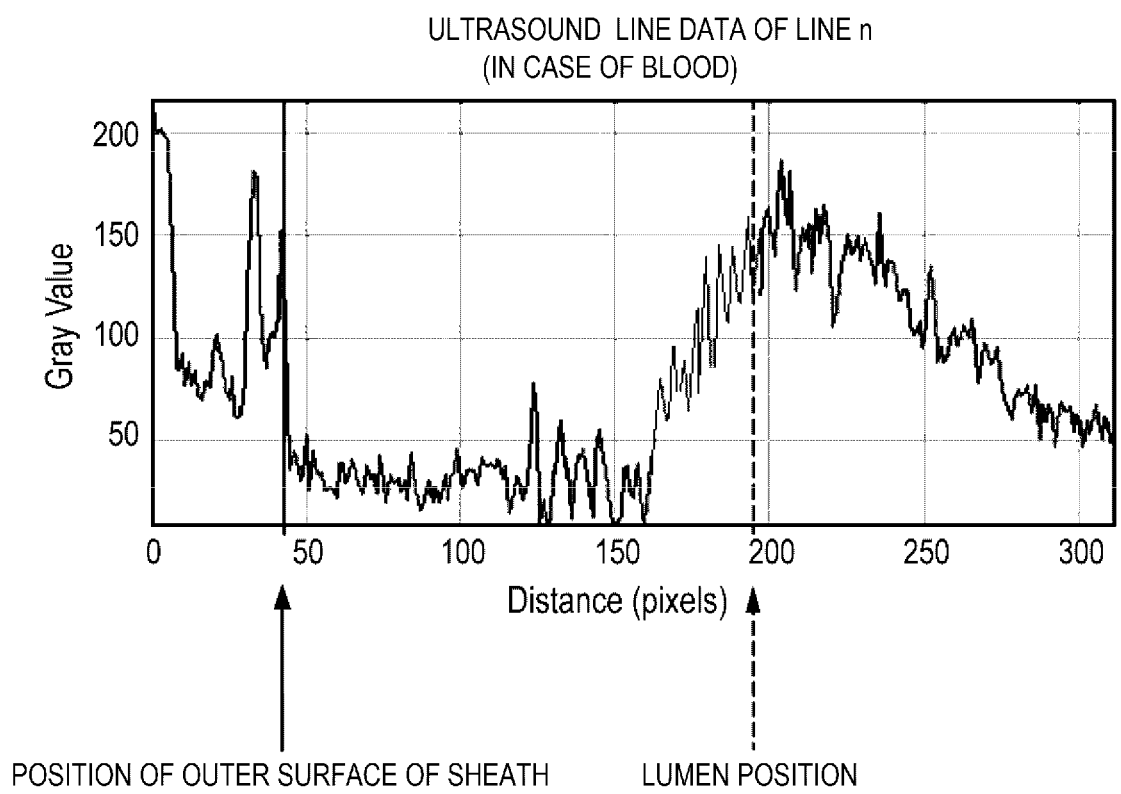
FIG. 7A is a diagram illustrating an example of ultrasound line data of a line n.

FIG. 7A illustrates the ultrasound line data of a line n (n is an arbitrary integer from 1 to 512) among the items of the ultrasound line data obtained by transmitting and receiving ultrasounds in a state where blood flows in a blood vessel.

As illustrated in FIG. 7A, since attenuation of ultrasounds is small in blood, when ultrasounds are transmitted and received in a state where blood flows in a blood vessel, an ultrasound signal having high strength can be received from the vicinity of the position of the lumen. In addition, the ultrasound signal having relatively high strength can be received from the inside of a blood vessel tissue (outside the position of the lumen).

Figure 7B:
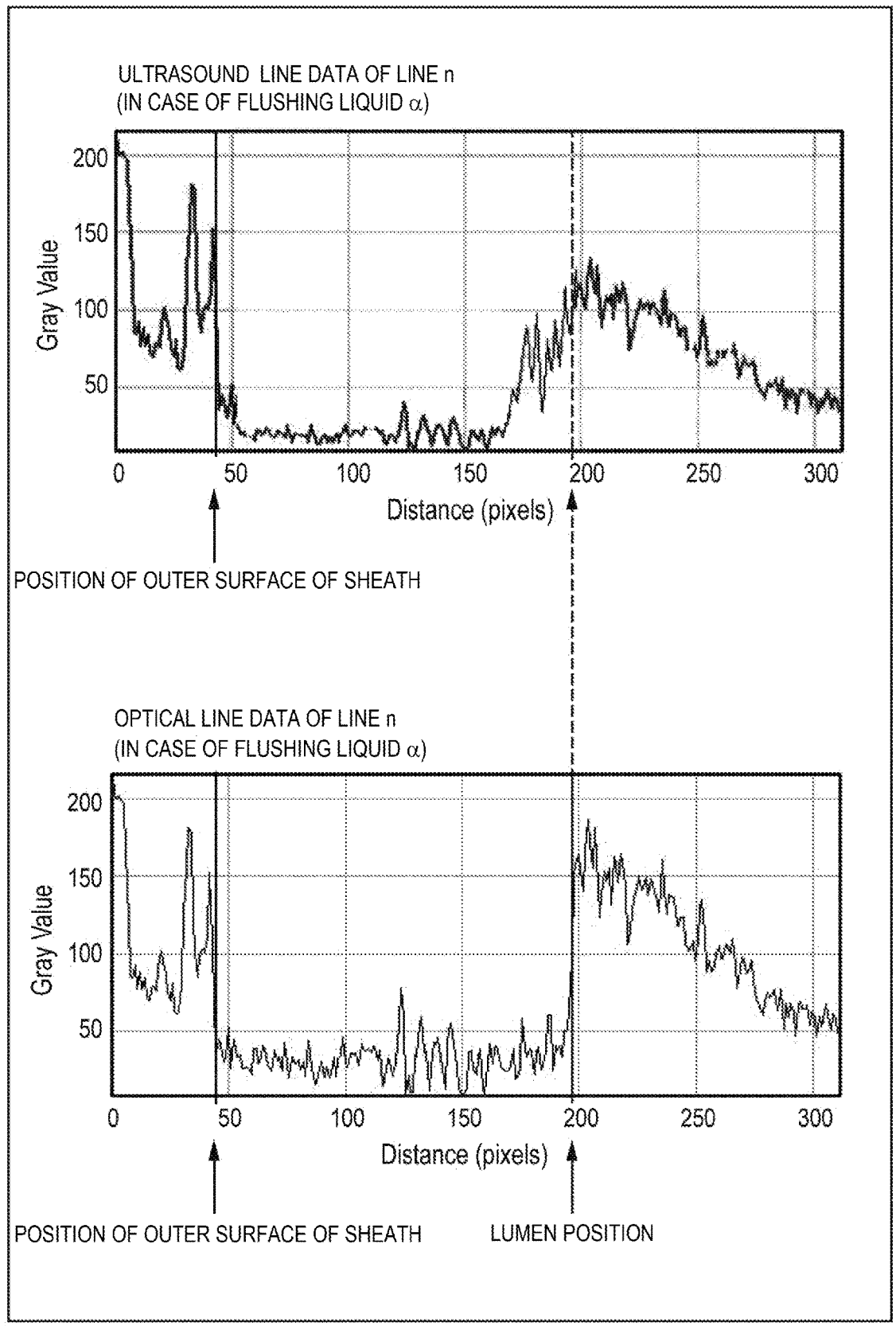
FIG. 7B is a diagram illustrating an example of the ultrasound line data of the line n when flushing is performed using a flushing liquid α.

Meanwhile, the upper side of the sheet in FIG. 7B illustrates the ultrasound line data of the line n (n is an arbitrary integer from 1 to 512) among the items of the ultrasound line data obtained by transmitting and receiving ultrasounds in a state where a flushing liquid α flows.

In addition, the lower side of the sheet in FIG. 7B illustrates the optical line data of the line n (n is an arbitrary integer from 1 to 512) among the items of the optical line data obtained by transmitting and receiving light in as state where the flushing liquid α flows.

As is clear through the comparison between the graph on the upper side of the sheet in FIG. 7B and the graph in FIG. 7A, since attenuation of ultrasounds in the flushing liquid α is greater than attenuation of ultrasounds in blood, strength of the ultrasound signal received in a state where the flushing liquid α flows is degraded compared to strength of the ultrasound signal received in a state where blood flows.

Figure 7C:
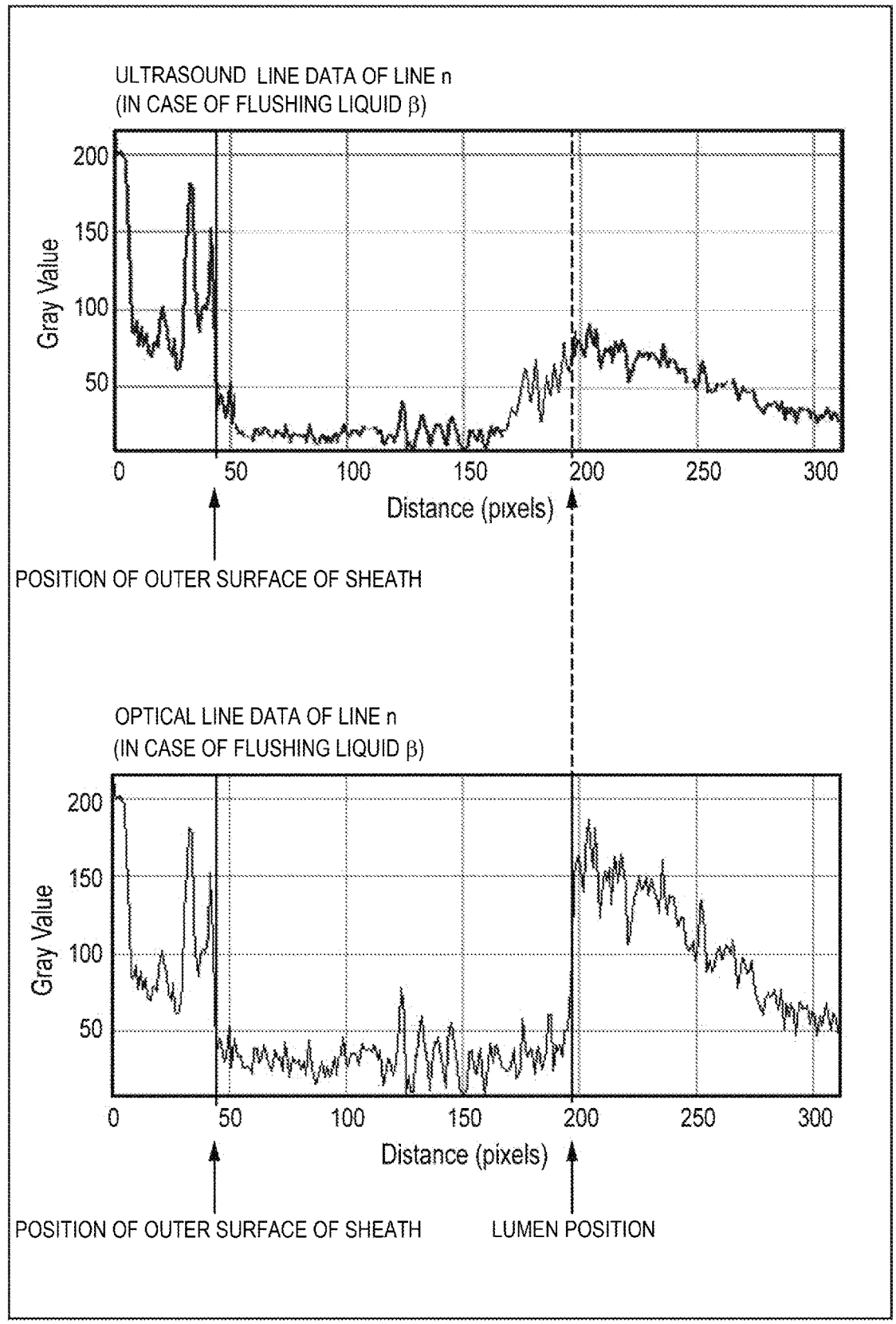
FIG. 7C is a diagram illustrating an example of the ultrasound line data of the line n when flushing is performed using a flushing liquid β.

Similarly, the upper side of the sheet in FIG. 7C illustrates the ultrasound line data of the line n (n is an arbitrary integer from 1 to 512) among the items of the ultrasound line data obtained by transmitting and receiving ultrasounds in a state where a flushing liquid β (another flushing liquid type different from the flushing liquid α) flows.

In addition, the lower side of the sheet in FIG. 7C illustrates the optical line data of the line n (n is an arbitrary integer from 1 to 512) among the items of the optical line data obtained by transmitting and receiving light in as state where the flushing liquid β flows.

As is clear through the comparison between FIG. 7B and FIG. 7C, the ultrasound signal is more likely to be affected than the optical signal. For example, signal strength of the ultrasound line data in a blood vessel tissue on the outer side from the position of the lumen differs depending on the type of the flushing liquid.

Therefore, when generating an ultrasound tomographic image by using the ultrasound line data, it is effective to change the gain with respect to the ultrasound line data depending on a state of whether blood flows or a flushing liquid flows in order to generate homogenous ultrasound tomographic images.

In addition, it is effective to change the gain with respect to the ultrasound line data depending on which type of the flushing liquid is used as the flushing liquid in accordance with the characteristics of attenuation of ultrasounds.

8. Flow of Ultrasound Line Data Gain Correction Processing

Subsequently, a flow of ultrasound line data gain correction processing in the ultrasound line data correction unit 513 will be described.

Figure 8A:
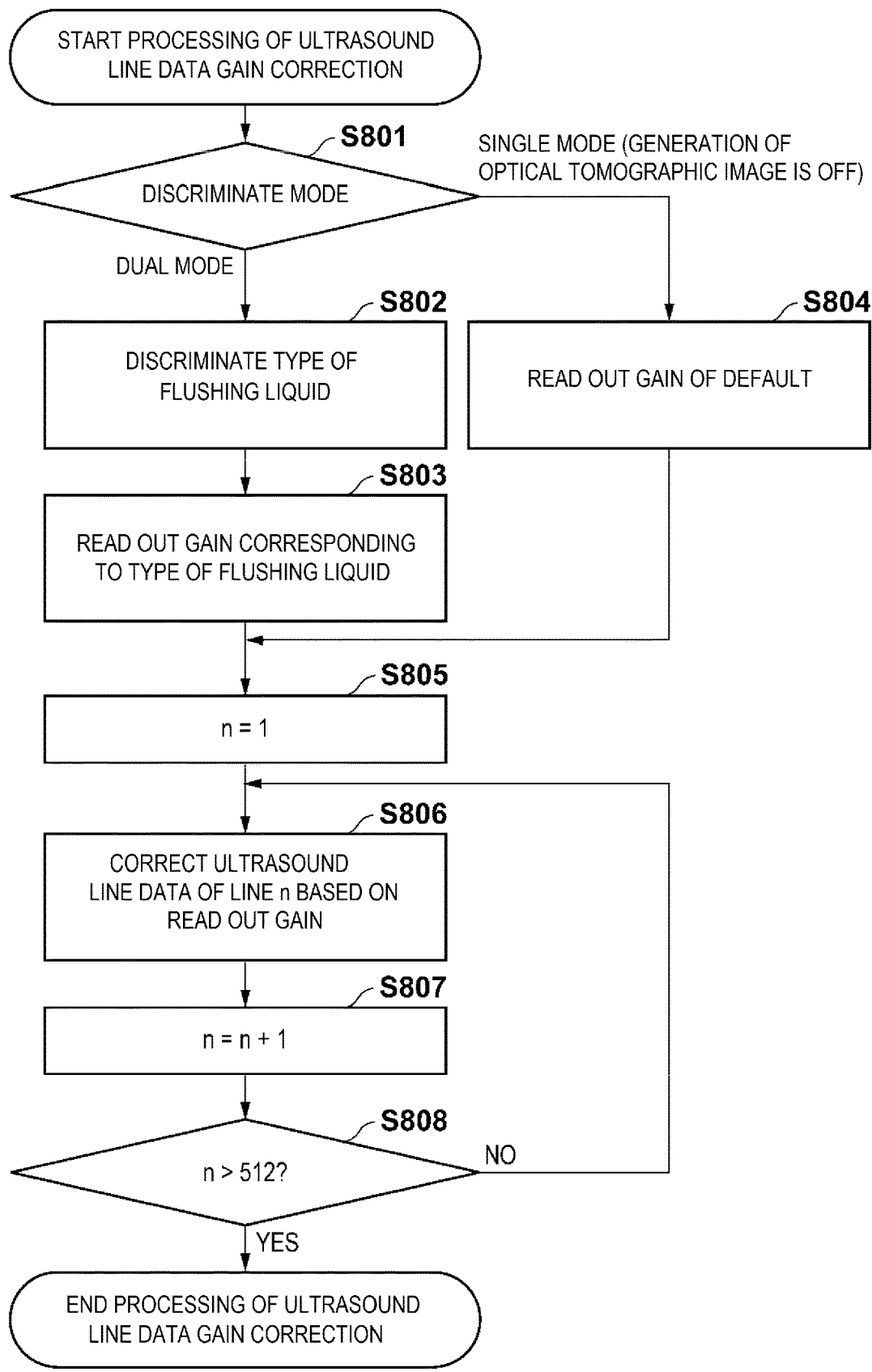
FIG. 8A is a flow chart illustrating a flow of ultrasound line data gain correction processing performed by an ultrasound line data correction unit.

FIG. 8A is a flow chart illustrating a flow of the ultrasound line data gain correction processing in the ultrasound line data correction unit 513. As illustrated in FIG. 8A, in Step S801, discrimination of a generation mode of a tomographic image is performed. In Step S801, when the dual mode (the mode for generating both the ultrasound tomographic image and the optical tomographic image) is selected, the processing proceeds to Step S802.

In Step S802, discrimination of the type of the flushing liquid is performed, and in Step S803, the gain is read out in accordance with the type of the flushing liquid which is subjected to discrimination performed in Step S802.

Meanwhile, in Step S801, when the single mode (the mode for generating only the ultrasound tomographic image) is selected, the processing proceeds to Step S804. In Step S804, a default gain is read out.

In Step S805, the numerical value "1" is input to the counter n, and in Step S806, the ultrasound line data of the line n (here, the line 1) is corrected based on the gain read out in Step S803 or Step S804.

In accordance with an exemplary embodiment, for example, the ultrasound line data is corrected based on the gain in accordance with the type of the flushing liquid in a state where the flushing liquid flows, and the ultrasound line data is corrected based on the default gain in a state where blood flows.

In Step S807, an increment of the counter n is performed, and in Step S808, it is determined whether or not the counter n is greater than 512. When it is determined that the counter n is equal to or less than 512 in Step S808, the processing returns to Step S806, and gain correction is performed with respect to 512 items of the ultrasound line data forming one frame.

Meanwhile, when gain correction is completed with respect to the 512 items of the ultrasound line data forming one frame, gain correction processing of the ultrasound line data ends.

As is clear from the above description, in the imaging apparatus 100 for diagnosis according to the present exemplary embodiment, it is constituted to arrange the ultrasound line data correction unit so as to perform gain correction for each item of the ultrasound line data. It is constituted to change the gain value in accordance with a state where blood flows or a state where the flushing liquid flows when performing gain correction. It is constituted to change the gain value in accordance with the type of the flushing liquid in a state where the flushing liquid flows.

Accordingly, despite the state of whether blood flows or the flushing liquid flows, or despite the type of the flushing liquid, homogenous ultrasound tomographic images can be generated.

In the first exemplary embodiment, the ultrasound line data in the entirety can be corrected by using the gain read out in Step S803 or Step S804. However, the present disclosure is not limited thereto. Since the IVUS has the characteristics which can measure a high depth region and data of the high depth region is important for the ultrasound line data, it may be constituted to limit the target of gain correction to the outer side of the position of the lumen (in a blood vessel tissue).

Figure 8B:
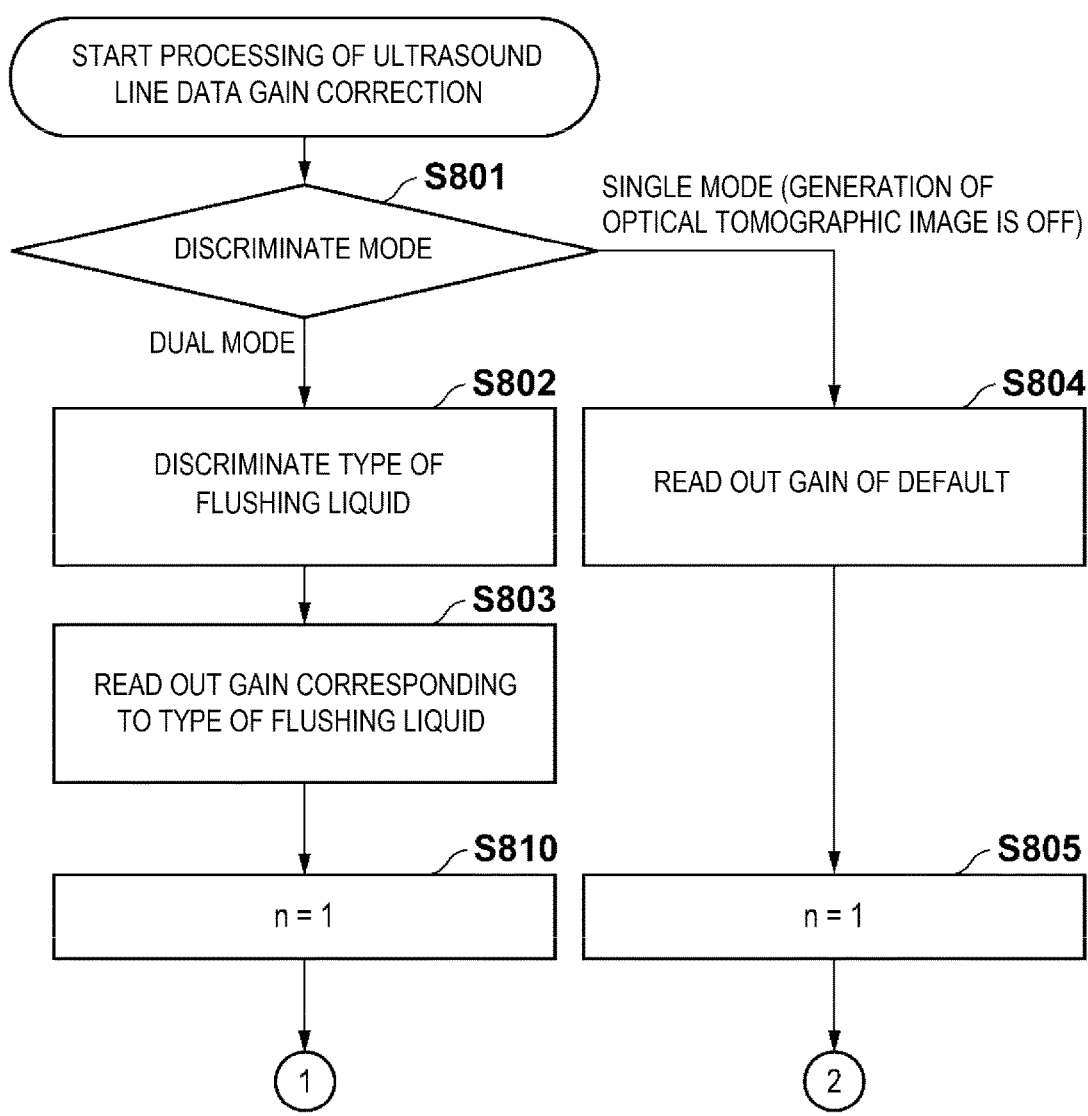
FIG. 8B is a flow chart illustrating another flow of the ultrasound line data gain correction processing performed by the ultrasound line data correction unit.
Figure 8C:
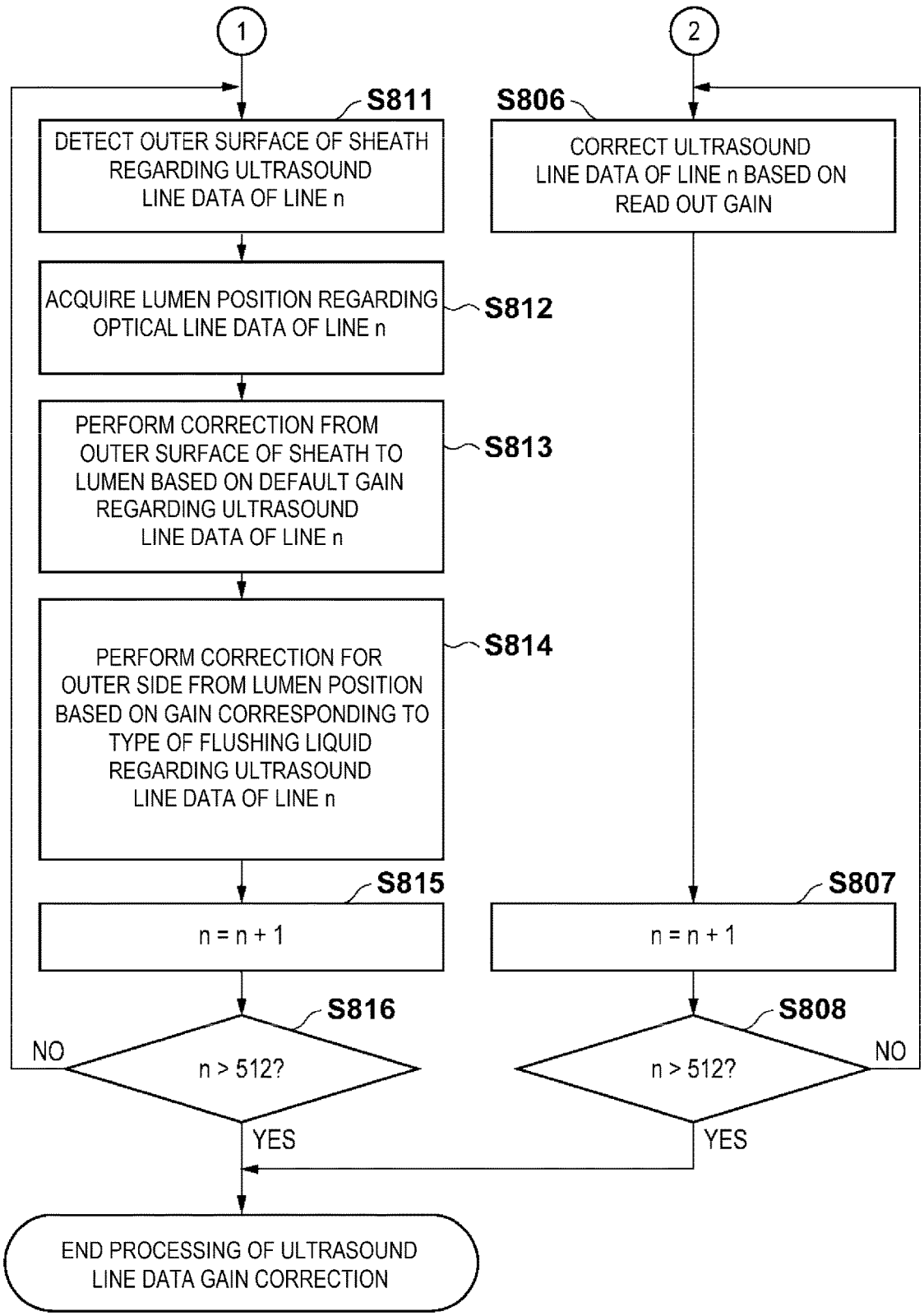
FIG. 8C is a flow chart illustrating further another flow of the ultrasound line data gain correction processing performed by the ultrasound line data correction unit.

FIGS. 8B and 8C are flow charts illustrating flows of the ultrasound line data gain correction processing in the ultrasound line data correction unit 513 of the imaging apparatus 100 for diagnosis according to the present exemplary embodiment. Regarding the processing similar to that in FIG. 8A, the same reference numeral and sign are applied and the description thereof will be omitted herein. Hereinafter, descriptions will be given focusing on the points different from those in FIG. 8A.

In FIG. 8B, in Step S810, in a case of the dual mode, the numerical value "1" is input to the counter n. In FIG. 8C, in Step S811, a position of an outer surface of the sheath is detected regarding the ultrasound line data of the line n (here, the line 1).

Moreover, in Step S812, the position of the lumen detected by the lumen position detection unit 503 is acquired regarding the optical line data of the line n (here, the line 1). It is constituted that the position of the lumen is detected based on the corresponding optical line data because the optical line data has the characteristics capable of detecting the position of the lumen more accurately.

In Step S813, correction is performed based on the default gain from the position of the outer surface of the sheath to the position of the lumen among the items of the ultrasound line data of the line n (here, the line 1).

In Step S814, the outer side from the position of the lumen is corrected based on the gain in accordance with the type of the flushing liquid among the items of the ultrasound line data of the line n (here, the line 1).

In Step S815, an increment of the counter n is performed, and in Step S816, it is determined whether or not the counter n is greater than 512. When it is determined that the counter n is equal to or less than 512 in Step S816, the processing returns to Step S811 and processing of Steps S811 to S815 are repeated with respect to 512 items of the ultrasound line data forming one frame.

Meanwhile, when gain correction is completed with respect to 512 items of the ultrasound line data forming one frame, gain correction processing of the ultrasound line data ends.

As is clear from the above description, in the imaging apparatus 100 for diagnosis according to the present exemplary embodiment, the imaging apparatus 100 can be constituted to arrange the ultrasound line data correction unit so as to perform gain correction for each item of the ultrasound line data. The imaging apparatus 100 can be constituted to change the gain value in accordance with a state where blood flows or a state where the flushing liquid flows when performing gain correction. The imaging apparatus 100 can be constituted to detect the position of the lumen based on the optical line data in a state where the flushing liquid flows. The imaging apparatus 100 can be constituted to perform correction based on the default gain from the outer surface of the sheath to the position of the lumen in a state where the flushing liquid flows, and to change the gain value in accordance with the type of the flushing liquid on the outer side from the position of the lumen.

Accordingly, despite the state of whether blood flows or the flushing liquid flows, or despite the type of the flushing liquid, homogenous ultrasound tomographic images can be generated.

In the first and second exemplary embodiments, the imaging apparatus 100 can be constituted to change the gain in accordance with the state of whether blood flows or the flushing liquid flows and in accordance with the type of the flushing liquid when the flushing liquid flows. However, the present disclosure is not limited thereto.

For example, even though the flushing liquid is the same, there is a case where correction of the gain needs to be performed further depending on the position of the imaging core 220 in the radial direction of a blood vessel. Therefore, in the present exemplary embodiment, the imaging apparatus 100 can be constituted to change the gain value in accordance with the position of the imaging core 220 in the radial direction of a blood vessel. Hereinafter, the present embodiment will be described in detail.

1. Operation of Imaging Core 220 and Description of Line Data

Figure 9:
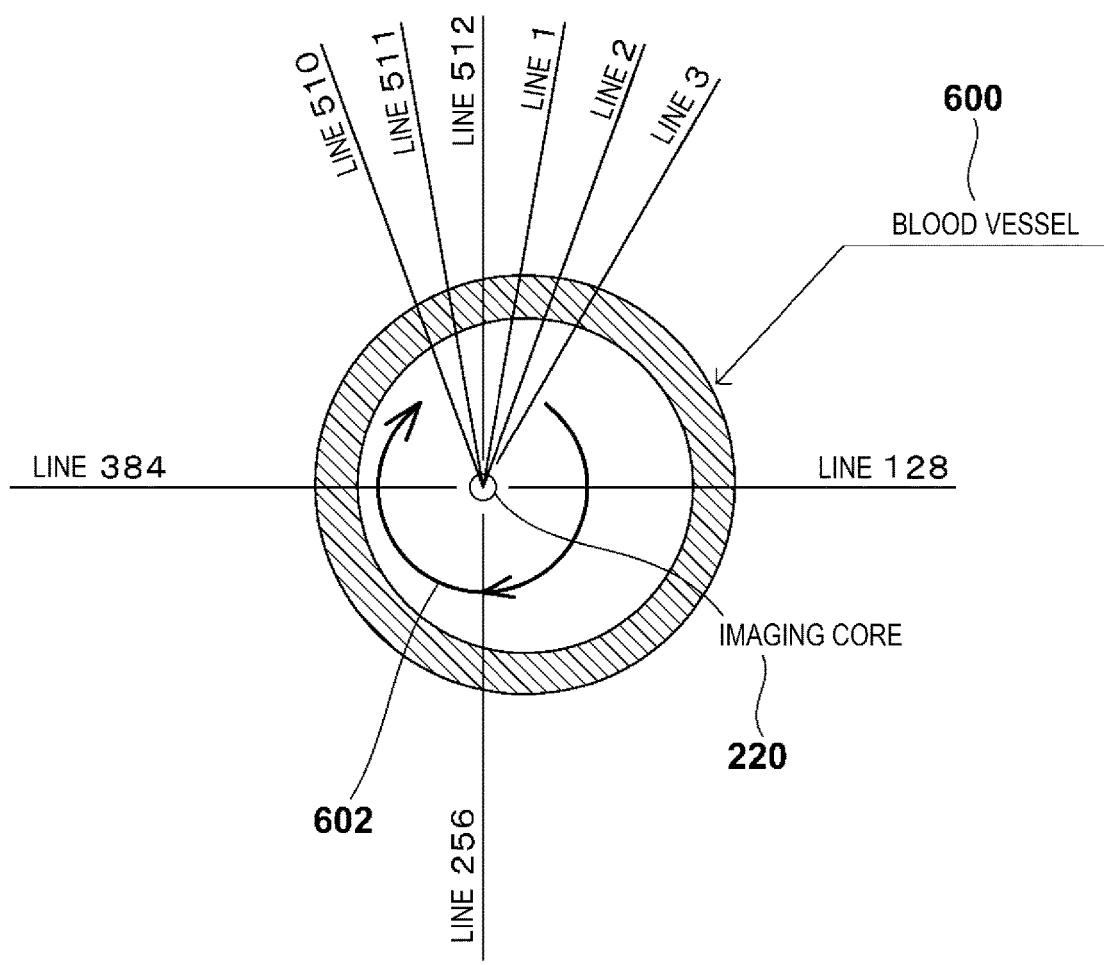
FIG. 9 is a diagram illustrating a data structure of another generated tomographic image.

FIG. 9 illustrates a state where the imaging core 220 is inserted through the inside of the blood vessel 600 is seen in the cross-sectional direction of the blood vessel 600. As illustrated in FIG. 9, in a state where the imaging core 220 is biased toward the left side of the sheet in the blood vessel 600, there is a significant difference between a distance from the position of the outer surface of the sheath in the ultrasound line data of a line 128 to the position of the lumen, and a distance from the position of the outer surface of the sheath in the ultrasound line data of a line 384 to the position of the lumen.

Here, in a state where the flushing liquid in which the attenuation factor of ultrasounds is significant flows, if the distance to the position of the lumen is long, there is an occurrence of remarkable attenuation until the ultrasounds reach the position of the lumen. In contrast, if the distance to the position of the lumen is short, there is a little occurrence of attenuation until the ultrasounds reach the position of the lumen.

Figure 10A:
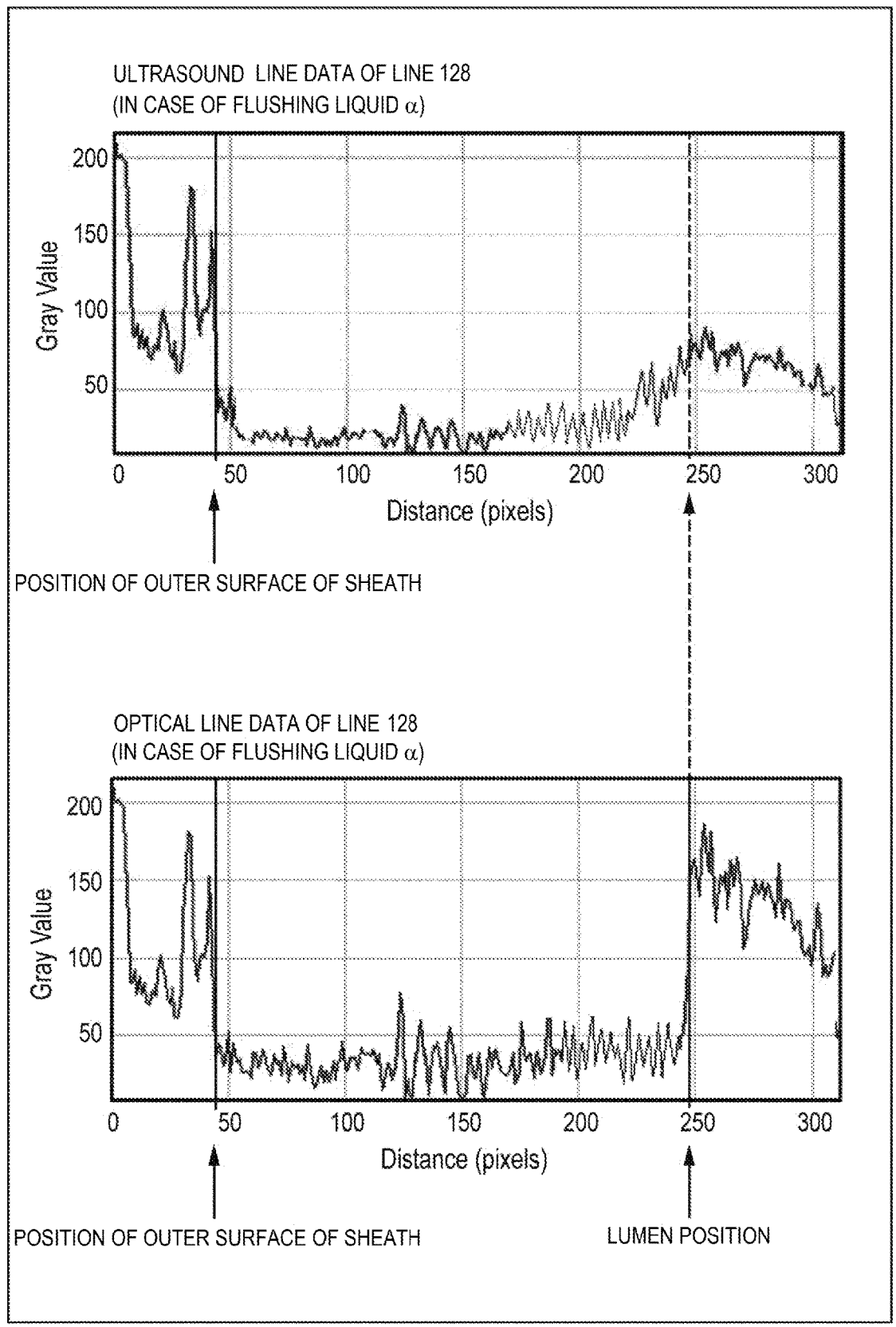
FIG. 10A is a diagram illustrating an example of the ultrasound line data of a line when flushing is performed using the flushing liquid α.

FIG. 10A is a diagram illustrating the ultrasound line data and the optical line data of the line 128. In contrast, FIG. 10B is a diagram illustrating the ultrasound line data and the optical line data of the line 384.

Figure 10B:
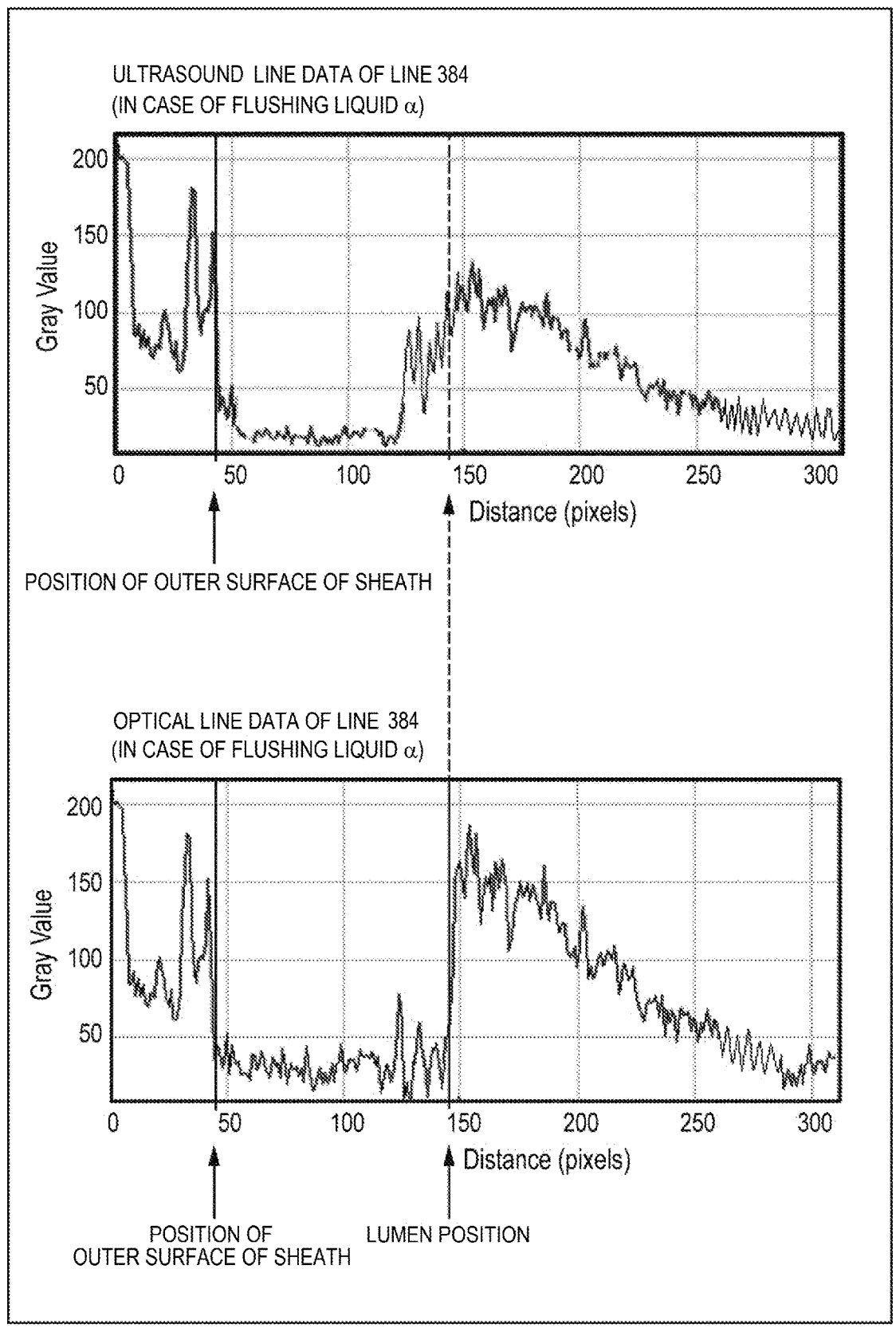
FIG. 10B is a diagram illustrating an example of the ultrasound line data of a line when flushing is performed using the flushing liquid α.

As is clear from the comparison between FIGS. 10A and 10B, signal strength of the ultrasound line data of the line 128 is smaller than signal strength of the ultrasound line data of the line 384. Meanwhile, signal strength of the optical line data of the line 128 and signal strength of the optical line data of the line 384 are substantially the same with each other.

Therefore, in the ultrasound line data, when it is intended to perform correction from the line 1 to the line 512 by using the same gain, the generated ultrasound tomographic image becomes dark on the right side of the sheet in FIG. 9 and becomes bright on the left side of the sheet.

In order to avoid such inhomogeneity, in the imaging apparatus for diagnosis according to the present exemplary embodiment, correction is performed while revising the gain value for each line in accordance with the distance from the position of the outer surface of the sheath to the position of the lumen.

2. Flow of Ultrasound Line Data Gain Correction Processing

Subsequently, a flow of ultrasound line data gain correction processing in the ultrasound line data correction unit 513 in the present exemplary embodiment will be described.

Figure 11A:
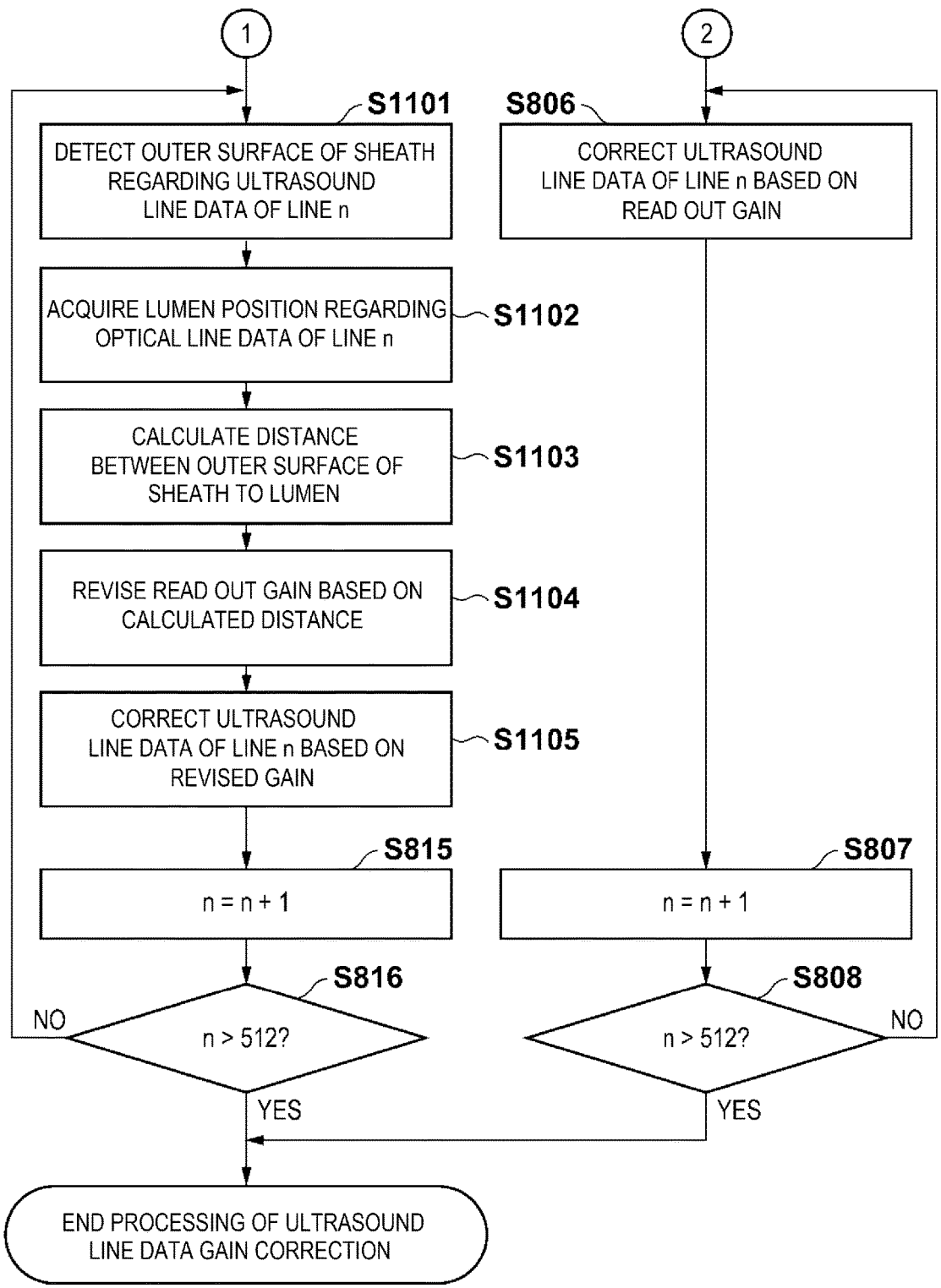
FIG. 11A is a flow chart illustrating a flow of the ultrasound line data gain correction processing performed by the ultrasound line data correction unit.

FIG. 11A is a flow chart illustrating the flow of the ultrasound line data gain correction processing in the ultrasound line data correction unit 513, together with FIG. 8B. Since FIG. 8B overlaps, descriptions thereof will be omitted. In addition, regarding FIG. 11A as well, the same reference numeral and sign are applied to processing similar to that in FIG. 8C, and descriptions thereof will be omitted herein.

Hereinafter, FIG. 11A will be described focusing on the points different from those in FIG. 8C.

In FIG. 11A, in Step S1101, the position of the outer surface of the sheath is detected regarding the ultrasound line data of the line n (here, the line 1). In addition, in Step S1102, the position of the lumen which is detected by the lumen position detection unit 503 is acquired regarding the optical line data of the line n (here, the line 1). It is constituted that the position of the lumen is detected based on the corresponding optical line data because the optical line data has the characteristics capable of detecting the position of the lumen more accurately.

In Step S1103, the distance from the outer surface of the sheath to the position of the lumen regarding the ultrasound line data of the line n (here, the line 1) is calculated.

In Step S1104, the gain which is read out in Step S803 is revised based on the distance calculated in Step S1103. As the revision method, for example, a coefficient proportional to the distance calculated in Step S1103 is integrated with the read out gain.

Hereinafter, since the processing in Steps S815 and S816 already has been described in FIG. 8A, the descriptions thereof will be omitted herein.

As is clear from the above description, in the imaging apparatus for diagnosis according to the present embodiment, the imaging apparatus can be constituted to arrange the ultrasound line data correction unit so as to perform gain correction for each item of the ultrasound line data. The imaging apparatus can be constituted to change the gain value in accordance with a state where blood flows a state where the flushing liquid flows when performing gain correction. The imaging apparatus can be constituted to detect the position of the lumen based on the optical line data in a state where the flushing liquid flows. The imaging apparatus can be constituted that the gain in accordance with the type of the flushing liquid is used in correction after being revised in accordance with the distance from the position of the outer surface of the sheath to the position of the lumen when being in a state where the flushing liquid flows.

Accordingly, despite the state of whether blood flows or the flushing liquid flows, despite the type of the flushing liquid, or despite the position of the imaging core, homogenous ultrasound tomographic images can be generated.

Figure 11B:
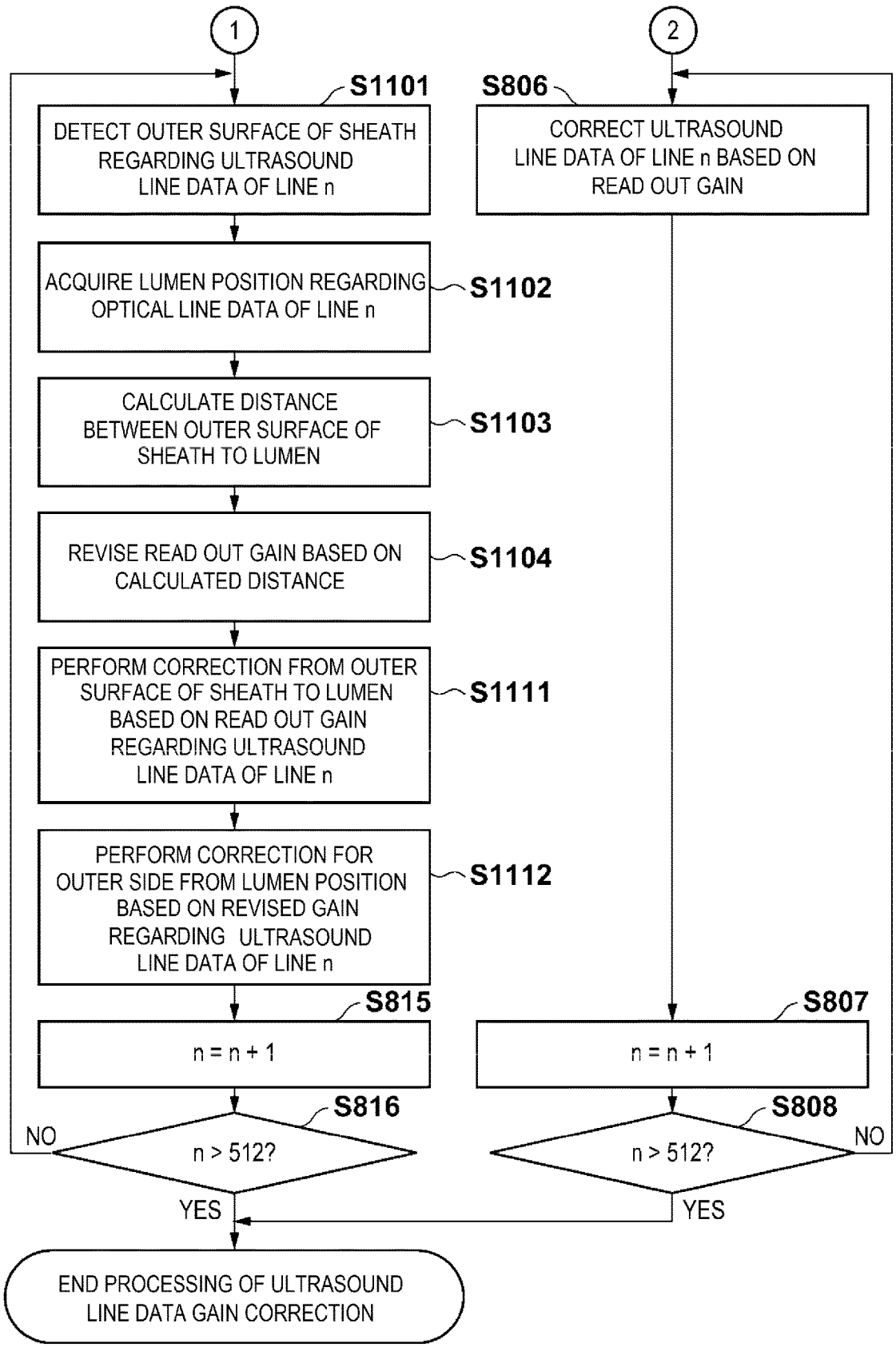
FIG. 11B is a flow chart illustrating another flow of the ultrasound line data gain correction processing performed by the ultrasound line data correction unit.

In the third exemplary embodiment, the imaging apparatus can be constituted to correct the ultrasound line data in the entirety after the gain read out in Step S803 or Step S804 is revised in accordance with the distance from the position of the outer surface of the sheath to the position of the lumen. However, the present disclosure is not limited thereto. Since the IVUS has the characteristics which can measure a high depth region and data of the high depth region is important for the ultrasound line data, the imaging apparatus can be may be constituted to limit the target of gain correction to the outer side of the position of the lumen (in a blood vessel tissue). FIG. 11B is a flow chart illustrating a flow of the ultrasound line data gain correction processing in the ultrasound line data correction unit 513 of the imaging apparatus 100 for diagnosis according to the present embodiment. Regarding the processing similar to that in FIG. 11A, the same reference numeral and sign are applied and the description thereof will be omitted herein. Hereinafter, descriptions will be given focusing on the points different from those in FIG. 11A.

In Step S1111, correction is performed based on the gain read out in Step S803 or Step S804 regarding the ultrasound line data from the position of the outer surface of the sheath to the position of the lumen. In accordance with an exemplary embodiment, for example, the ultrasound line data can be corrected based on the gain in accordance with the type of the flushing liquid in a state where the flushing liquid flows, and the ultrasound line data is corrected based on the default gain in a state where blood flows.

Moreover, in Step S1112, correction is performed based on the gain revised in Step S1104 regarding the ultrasound line data on the outer side from the position of the lumen. For example, correction is performed after the gain in accordance with the type of the flushing liquid is revised in accordance with the distance from the position of the outer surface of the sheath to the position of the lumen in a state where the flushing liquid flows. In addition, correction is performed after the default gain is revised in accordance with the distance from the position of the outer surface of the sheath to the position of the lumen in a state where blood flows.

As is clear from the above description, in the imaging apparatus 100 for diagnosis according to the present exemplary embodiment, the imaging apparatus 100 can be constituted to arrange the ultrasound line data correction unit so as to perform gain correction for each item of the ultrasound line data. The imaging apparatus 100 can be constituted to change the gain value in accordance with a state where blood flows or a state where the flushing liquid flows when performing gain correction. The imaging apparatus 100 cab be constituted to detect the position of the lumen based on the optical line data in a state where the flushing liquid flows. The imaging apparatus 100 can be constituted to perform correction from the position of the outer surface of the sheath to the position of the lumen based on the gain in accordance with the type of the flushing liquid, and it is constituted that the gain in accordance with the type of the flushing liquid is used in correction after being revised in accordance with the distance from the position of the outer surface of the sheath to the position of the lumen regarding the outer side from the position of the lumen, in a state where the flushing liquid flows.

Accordingly, despite the state of whether blood flows or the flushing liquid flows, despite the type of the flushing liquid, or despite the position of the imaging core, homogenous ultrasound tomographic images can be generated.

In the first to fourth exemplary embodiments, discrimination of the generation mode of a tomographic image is performed when determining the state of whether blood flows or the flushing liquid flows (for example, determining the state of whether only the ultrasound tomographic image can be generated or both the ultrasound tomographic image and the optical tomographic image can be generated). However, the present disclosure is not limited thereto. The imaging apparatus 100 may be constituted to determine the state by discriminating that the flushing device for causing the flushing liquid to flow is in operation, or by reading out various types of setting data (setting and the like of the flushing liquid) input by a user.

In the first and second exemplary embodiments, the imaging apparatus 100 can be constituted to change the gain value. However, the present disclosure is not limited thereto. The imaging apparatus 100 may be constituted to change signal strength of ultrasounds transmitted by the ultrasound transmitting and receiving unit 310.

The detailed description above describes an imaging apparatus for diagnosis, and a program. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis generating a first tomographic image and a second tomographic image inside a lumen of a measurement subject body, the apparatus comprising:
   a transmitter and receiver comprising a first transmitter and receiver and a second transmitter and receiver, the first transmitter and receiver configured to perform transmission and reception of an ultrasound signal when rotating in the lumen of the measurement subject body, and the second transmitter and receiver configured to perform transmission and reception of an optical signal when rotating in the lumen of the measurement body; and
   a processor configured to:
      receive an input by a user to generate both the first tomographic image and the second tomographic image or to generate only the first tomographic image, the first tomographic image generated using the ultrasound signal and the second tomographic image generated using the optical signal; and
      execute a gain correction for changing a gain with respect to an ultrasound line data generated based on the ultrasound signal received by the first transmitter and receiver at a time of generating the first tomographic image based on the ultrasound line data, in accordance with the input by the user to generate both the first tomographic image and the second tomographic image or to generate only the first tomographic image.

2. The imaging apparatus for diagnosis according to claim 1, wherein the processor is further configured to:
   receive an input by the user of a type of a liquid inserted into the lumen when the transmitter and receiver moves in the axial direction while rotating in the lumen of the measurement subject body where the input by the user is to generate both the first tomographic image and the second tomographic image; and
   execute the gain correction, which includes changing the gain in accordance with the type of the liquid.

3. The imaging apparatus for diagnosis according to claim 2, wherein the type of the liquid is classified in accordance with characteristics of attenuation of the ultrasound signal.

4. The imaging apparatus for diagnosis according to claim 2, wherein the lumen of the measurement subject body is a blood vessel, and wherein the imaging apparatus for diagnosis further comprises:
   a first detector configured to detect a position of the lumen of the blood vessel based on the optical signal received by the second transmitter and receiver where the input by the user is to generate both the first tomographic image and the second tomographic image; and
   wherein the processor is configured to change the gain for a region detected outside of the position of the lumen by the first detector.

5. The imaging apparatus for diagnosis according to claim 4, comprising:
   a second detector configured to detect a position of an outer surface of a sheath in which the transmitter and receiver is interpolated, based on the ultrasound signal received by the first transmitter and receiver; and wherein the processor is configured to:
calculate a distance between the position of the lumen detected by the first detector and the position of the outer surface of the sheath detected by the second detector; and
revise the gain in accordance with the distance calculated.

6. The imaging apparatus for diagnosis according to claim 5, wherein the processor is configured to:
perform a revision to cause the gain to increase as the distance calculated increases.

7. The imaging apparatus for diagnosis according to claim 2,
wherein the first tomographic image is an intra-vascular and ultrasound the second tomographic image is an optical coherence tomography; and
the input by the user of the type of liquid being information on a flushing liquid, and wherein the input by the user to generate both the first tomographic image and the second tomographic image or to generate only the first tomographic image and the input of the user of the type of liquid is input by the user via an operation panel.

8. The imaging apparatus for diagnosis according to claim 1,
wherein the lumen of the measurement subject body is a blood vessel; and
wherein the imaging apparatus for diagnosis further comprises:
a first detector configured to detect a position of the lumen of the blood vessel based on the optical signal received by the second transmitter and receiver where the input by the user is to generate both the first tomographic image and the second tomographic image, and
wherein the gain correction changes the gain for a region detected outside of the position of the lumen by the first detector.

9. The imaging apparatus for diagnosis according to claim 8, comprising:
a second detector configured to detect a position of an outer surface of a sheath in which the transmitter and receiver is interpolated, based on the ultrasound signal received by the first transmitter and receiver; and
wherein the processor is configured to:
calculate a distance between the position of the lumen detected by the first detector and the position of the outer surface of the sheath detected by the second detector; and
revise the gain in accordance with the distance calculated.

10. The imaging apparatus for diagnosis according to claim 9, wherein the processor is configured to:
perform a revision to cause the gain to increase as the distance calculated increases.

11. A non-transitory computer readable medium configured to store a program for causing the processor of the imaging apparatus for diagnosis according to claim 1 to:
receive the input by the user to generate both the first tomographic image or to generate only the first tomographic image; and
execute the gain correction for changing a gain with respect to an ultrasound line data generated based on the ultrasound signal received by the first transmitter and receiver at a time of generating the first tomographic image based on the ultrasound line data received, in accordance with the input by the user to generate both the first tomographic image and the second tomographic image or to generate only the first tomographic image.

12. An imaging apparatus for diagnosis generating a first tomographic image and a second tomographic image inside a lumen of a measurement subject body, the apparatus comprising:
a transmitter and receiver comprising a first transmitter and receiver and a second transmitter and receiver, the first transmitter and receiver configured to perform transmission and reception of an ultrasound signal when rotating in the lumen of the measurement subject body, and the second transmitter and receiver configured to perform transmission and reception of an optical signal when rotating in the lumen of the measurement body; and
a processor configured to:
receive an input by a user to generate both the first tomographic image and the second tomographic image or to generate only the first tomographic image, the first tomographic image generated using the ultrasound signal and the second tomographic image generated using the optical signal; and
change a signal strength of the ultrasound signal transmitted by the first transmitter and receiver, in accordance with the input by the user to generate both the first tomographic image and the second tomographic image or to generate only the first tomographic image.

13. The imaging apparatus for diagnosis according to claim 12, wherein the lumen of the measurement subject body is a blood vessel.

14. The imaging apparatus for diagnosis according to claim 13,
wherein the first tomographic image is an intra-vascular ultrasound and the second tomographic image is an optical coherence tomography; and
the input by the user of the type of liquid being information on a flushing liquid, and wherein the input by the user to generate both the first tomographic image and the second tomographic image or to generate only the first tomographic image and the input of the type of liquid is input by the user via an operation panel.

15. A non-transitory computer readable medium configured to store a program for causing the processor of the imaging apparatus for diagnosis according to claim 12 to:
receive the input by the user to generate both the first tomographic image and the second tomographic image or to generate only the first tomographic image; and
change the signal strength of the ultrasound signal transmitted by the first transmitter and receiver, in accordance with the input by the user to generate both the first tomographic image and the second tomographic image or to generate only the first tomographic image.

16. A method of controlling an imaging apparatus for diagnosis generating a first tomographic image and a second tomographic image inside a lumen of a measurement subject body by using an ultrasound signal which is transmitted and received by a first transmitter and receiver and an optical signal which is transmitted and received by a second transmitter and receiver in a case where a transmitter and receiver in which the first transmitter and receiver performing transmission and reception of the ultrasound signal and the second transmitter and receiver performing transmission and reception of the optical signal are disposed moves in an axial direction while rotating in the lumen of the measurement subject body, the method comprising:

receiving an input by a user to generate both the first tomographic image and the second tomographic image or to generate only the first tomographic image, the first tomographic image generated using the ultrasound signal and the second tomographic image generated using the optical signal; and changing a gain with respect to an ultrasound line data generated based on the ultrasound signal received by the first transmitter and receiver at a time of generating the first tomographic image based on the ultrasound line data received by the first transmitter and receiver.

17. The method according to claim 16, comprising:

receiving an input by the user of a type of a liquid inserted into the lumen when the transmitter and receiver moves in the axial direction while rotating in the lumen of the measurement subject body where the input by the user is to generate both the first tomographic image and the second tomographic image; and changing the gain in accordance with the type of the liquid.

18. The method according to claim 17, wherein the lumen of the measurement subject body is a blood vessel.

19. The method according to claim 18, comprising:

detecting a position of the lumen of the blood vessel based on the optical signal received by the second transmitter and receiver where the input by the user is to generate both the first tomographic image and the second tomographic image, and changing the gain for a region detected outside of the position of the lumen.

* * * * *